(12) United States Patent
Sato et al.

(10) Patent No.: US 11,344,271 B2
(45) Date of Patent: May 31, 2022

(54) X-RAY DIAGNOSTIC APPARATUS AND X-RAY TUBE HOLDING DEVICE

(71) Applicant: CANON MEDICAL SYSTEMS CORPORATION, Otawara (JP)

(72) Inventors: Motohiro Sato, Nasushiobara (JP); Hidesuke Tomura, Otawara (JP); Koichi Kaminaga, Shioya (JP); Toshiaki Kondo, Yaita (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/883,091

(22) Filed: May 26, 2020

(65) Prior Publication Data

US 2020/0297301 A1 Sep. 24, 2020

Related U.S. Application Data

(63) Continuation of application No. PCT/JP2018/043451, filed on Nov. 26, 2018.

(30) Foreign Application Priority Data

Nov. 28, 2017 (JP) .............................. JP2017-227942

(51) Int. Cl.
*A61B 6/00* (2006.01)
*A61B 6/04* (2006.01)

(52) U.S. Cl.
CPC .............. *A61B 6/5229* (2013.01); *A61B 6/04* (2013.01); *A61B 6/461* (2013.01); *A61B 6/54* (2013.01)

(58) Field of Classification Search
CPC ......... A61B 6/5229; A61B 6/04; A61B 6/461; A61B 6/54; A61B 6/4452
See application file for complete search history.

(56) References Cited

U.S. PATENT DOCUMENTS

| 7,634,308 | B2 | 12/2009 | Ogawa |
| 2004/0127789 | A1 | 7/2004 | Ogawa |
| 2017/0055925 | A1* | 3/2017 | Lee .......................... A61B 6/545 |

(Continued)

FOREIGN PATENT DOCUMENTS

| JP | 2003-230556 A | 8/2003 |
| JP | 2004-209239 A | 7/2004 |
| JP | 2009-279295 A | 12/2009 |

(Continued)

OTHER PUBLICATIONS

International Search Report dated Feb. 19, 2019 in PCT/JP2018/043451 filed on Nov. 26, 2018, 2 pages (Continued)

*Primary Examiner* — Courtney D Thomas
(74) *Attorney, Agent, or Firm* — Oblon, McClelland, Maier & Neustadt, L.L.P.

(57) ABSTRACT

An X-ray diagnostic apparatus according to an embodiment has a display configured to superimpose and display a plurality of X-ray irradiation ranges for generating a long range X-ray image on an image indicating a subject; and a display controller configured to change, based on an operation of a user, a position of an overlap region which is displayed on the display and at which the X-ray irradiation ranges which are adjacent to each other are overlapped.

17 Claims, 32 Drawing Sheets

(56) References Cited

U.S. PATENT DOCUMENTS

2019/0343479 A1* 11/2019 Sato .................... A61B 6/5241

FOREIGN PATENT DOCUMENTS

| | | |
|---|---|---|
| JP | 2013-106708 A | 6/2013 |
| JP | 2014-68578 A | 4/2014 |
| JP | 5634744 B2 | 12/2014 |
| JP | 2016-034300 A | 3/2016 |
| WO | WO 2014/132361 A1 | 9/2014 |

OTHER PUBLICATIONS

International Preliminary Report on Patentability and Written Opinion dated Jun. 11, 2020 in PCT/JP2018/043451 (submitting English translation only), 8 pages.

Japanese Office Action dated Oct. 26, 2021 in Japanese Patent Application No. 2019-557217, 7 pages.

Japanese Office Action dated Feb. 4, 2022, issued in Japanese Application No. 2019-557217.

* cited by examiner

X-RAY DIAGNOSTIC APPARATUS AND X-RAY TUBE HOLDING DEVICE

CROSS REFERENCE TO RELATED APPLICATIONS

This application is a Continuation of International Application No. PCT/JP2018/043451, filed on Nov. 26, 2018, the entire contents of which is hereby incorporated by reference.

FIELD

Embodiments of the present invention relate to an X-ray diagnostic apparatus and an X-ray tube holding device.

BACKGROUND

An X-ray diagnostic apparatus which irradiates a subject with X-rays and detects the X-rays transmitted through the subject to perform X-ray imaging is widely used in the medical field. One of imaging methods of the X-ray diagnostic apparatus is long range imaging. The long range imaging is an imaging method in which, since an imaging range is limited in one time of X-ray imaging using an X-ray tube, X-ray imaging is performed a plurality of times to generate a plurality of X-ray images at different imaging positions, and these plurality of X-ray images are synthesized, to thereby widen the imaging range.

However, in the long range imaging, the plurality of X-ray images have to be synthesized, and when synthesizing the X-ray images, there is a need to perform image processing such as blend processing on an overlap region at which different X-ray images are combined and superimposed. Specifically, in order to prevent generation of a sense of incompatibility in the X-ray images caused by the combination of the different X-ray images, an image based on the plural different X-ray images is created as the overlap region. However, with the use of such image processing, there is a risk such that the X-ray images are blurred, so that it is not preferable to perform the blend processing on a region of interest of a user.

DETAILED DESCRIPTION

Figure 1:
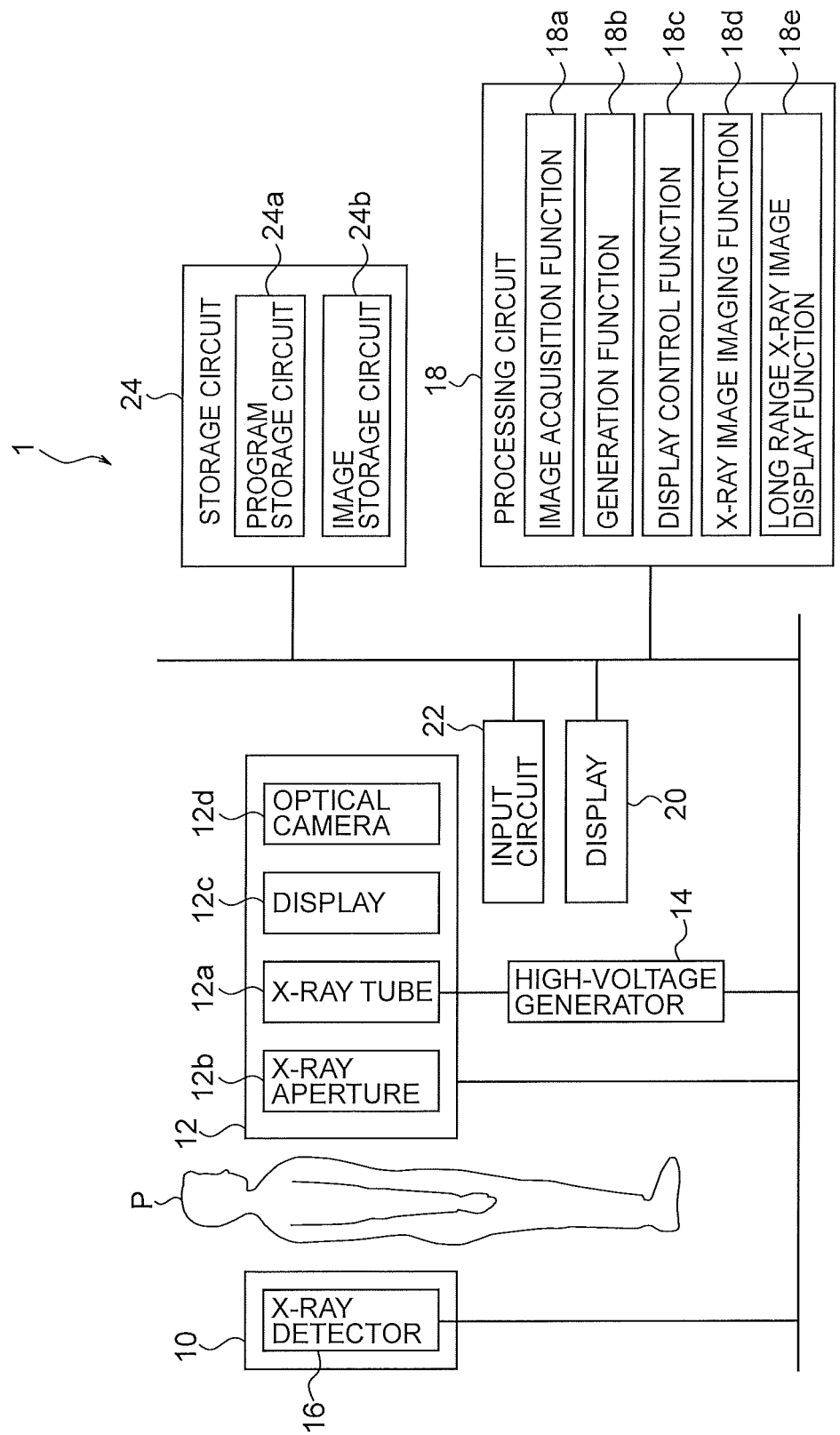
FIG. 1 is a block diagram explaining an entire configuration of an X-ray diagnostic apparatus according to a first embodiment (a case of standing position)

Hereinafter, an X-ray diagnostic apparatus, and an X-ray tube holding device according to the present embodiment will be described while referring to the drawings. Note that in the description hereinbelow, components having substantially the same functions and configurations will be denoted by the same reference numerals, and duplicated explanation will be made only in a necessary case.

First Embodiment

FIG. 1 is a block diagram explaining an entire configuration of an X-ray diagnostic apparatus 1 according to a first embodiment. The X-ray diagnostic apparatus 1 illustrated in FIG. 1 is configured by including mainly a stand 10, an X-ray tube holding device 12, a high-voltage generator 14, an X-ray detector 16, a processing circuit 18, a display 20, an input circuit 22, and a storage circuit 24. Further, the X-ray tube holding device 12 according to the present embodiment is configured by including an X-ray tube 12a, an X-ray aperture 12b, a display 12c, and an optical camera 12d.

In front of the stand 10, a subject P in a standing state is positioned. In the X-ray diagnostic apparatus 1 according to the present embodiment, it is possible to perform partial imaging of the standing subject P in one time of X-ray imaging which uses the X-ray detector 16 of the stand 10 and the X-ray tube 12a of the X-ray tube holding device 12. Accordingly, the stand 10 is configured to be able to move in the longitudinal direction in conjunction with the X-ray tube holding device 12, and it can perform X-ray imaging at plural different locations to generate X-ray images at the plural different locations. Specifically, in the X-ray diagnostic apparatus 1 according to the present embodiment, it is possible to synthesize X-ray images at plural locations, to thereby generate a long range X-ray image.

The X-ray tube 12a of the X-ray tube holding device 12, to which a high voltage and a filament current are supplied from the high-voltage generator 14 under control of the processing circuit 18, generates X-rays on the basis of the high voltage and the filament current. The X-ray aperture 12b of the X-ray tube holding device 12 performs focusing of the X-rays generated by the X-ray tube 12a, thereby controlling a range of X-rays to be applied to the subject P. Specifically, it is possible to narrow the irradiation range of X-rays by narrowing the aperture of the X-ray aperture 12b, and on the contrary, it is possible to widen the irradiation range of X-rays by opening the aperture of the X-ray aperture 12b. The degree of narrowing of the X-ray aperture 12b is controlled by a control signal from the processing circuit 18 based on an instruction made by an operator, for example.

The display 12c of the X-ray tube holding device 12 displays various kinds of information regarding the X-ray diagnostic apparatus 1 or an image imaged by the optical camera 12d to the operator. Further, in the present embodiment, the display 12c is configured by a touch panel, and the operator can input various kinds of instructions into the X-ray diagnostic apparatus 1. Specifically, this display 12c corresponds to an input accepter in the present embodiment.

The optical camera 12d of the X-ray tube holding device 12 is an imaging device capable of performing imaging of an image indicating the subject P, and is a wide-angle imaging device capable of performing imaging of the whole body of the subject P in the present embodiment in particular. Further, the optical camera 12d is not an imaging device for X-ray imaging, but is an optical imaging device which performs imaging by detecting light and converting the light into an electrical signal.

The high-voltage generator 14 makes, based on a control instruction made by the processing circuit 18, a high voltage and a filament current in accordance with an X-ray condition to be generated, and supplies the high voltage and the filament current to the X-ray tube 12a of the X-ray tube holding device 12, to thereby make the X-ray tube 12a generate X-rays.

The X-ray detector 16 is configured by, for example, a flat panel detector (FPD) having a plurality of pixels which are arrayed two-dimensionally, in which each of the pixels detects an X-ray from the X-ray tube 12a transmitted through the subject P, converts the detected X-ray into an electrical signal, and further converts the electrical signal into a digital signal. This digital signal is output to the processing circuit 18.

The processing circuit 18 is a control circuit that performs overall control of the X-ray diagnostic apparatus 1, and is also an arithmetic circuit that performs various kinds of arithmetic operations. For example, the processing circuit 18 according to the present embodiment includes an image acquisition function 18a, a generation function 18b, a display control function 18c, an X-ray image imaging function 18d, and a long range X-ray image display function 18e. The image acquisition function 18a corresponds to an image acquirer according to the present embodiment, the generation function 18b corresponds to a generator in the present embodiment, the display control function 18c corresponds to a display controller in the present embodiment, the X-ray image imaging function 18d corresponds to an X-ray image imager in the present embodiment, and the long range X-ray image display function 18e corresponds to a long range X-ray image display in the present embodiment.

In the embodiment in FIG. 1, respective processing functions performed in the image acquisition function 18a, the generation function 18b, the display control function 18c, the X-ray image imaging function 18d, and the long range X-ray image display function 18e are stored in a program storage circuit 24a of the storage circuit 24, in forms of programs capable of being executed by a computer. The processing circuit 18 is a processor that reads the programs from the program storage circuit 24a of the storage circuit 24 and executes the programs to thereby realize the functions corresponding to the respective programs. In other words, the processing circuit in a state of having read the respective programs has the respective functions illustrated in the processing circuit 18 in FIG. 1. Note that FIG. 1 is illustrated such that the image acquisition function 18a, the generation function 18b, the display control function 18c, the X-ray image imaging function 18d, and the long range X-ray image display function 18e are realized by the single processing circuit 18. However, a plurality of independent processors may be combined to configure the processing circuit 18 so that the respective processors execute the programs to thereby realize the functions.

The display 20 displays various kinds of images and information. For example, the display 20 displays a medical image (X-ray image) generated by the processing circuit 18, a GUI (Graphical User Interface) or the like for accepting various kinds of operations from an operator. In particular, in the present embodiment, the display 20 displays a long range X-ray image generated by the generation function 18b of the processing circuit 18. In the present embodiment, the display 20 is configured by, for example, a liquid crystal display, a CRT (Cathode Ray Tube) display, or the like.

The input circuit 22 accepts various kinds of input operations from the operator, converts the accepted input operation into an electrical signal, and outputs the electrical signal to the processing circuit 18. For example, the input circuit 22 is realized by a mouse, a keyboard, a trackball, a manual switch, a foot switch, a button, a joystick, or the like. In the present embodiment, it is also possible to configure the input circuit 22 by configuring the display 12c and the display 20 with the use of touch panels.

The storage circuit 24 is realized by, for example, a semiconductor memory element such as a RAM (Random Access Memory) or a flash memory, a hard disk, an optical disk, or the like. The storage circuit 24 according to the present embodiment is configured by including, for example, a program storage circuit 24a and an image storage circuit 24b. The program storage circuit 24a stores the various kinds of programs to be executed by the processing circuit 18 and the like, as described above. The image storage circuit 24b stores data regarding various kinds of images. In the present embodiment, the image storage circuit 24b stores X-ray images generated based on X-rays detected by the X-ray detector 16, and stores images imaged by the optical camera 12d of the X-ray tube holding device 12, for example.

As described above, the processing circuit 18 is configured by, for example, the processor in the present embodiment. The word processor here means, for example, a CPU (Central Processing Unit), a GPU (Graphics Processing Unit), or a circuit such as an application specific integrated circuit (ASIC), a programmable logic device (for example, a simple programmable logic device: SPLD), a complex programmable logic device (CPLD), and a field programmable gate array (FPGA). The processor realizes the functions by reading and executing the programs stored in the program storage circuit 24a of the storage circuit 24. Note that instead of storing the programs in the program storage circuit 24a of the storage circuit 24, the programs may be directly installed in a circuit of the processor. In this case, the processor reads and executes the programs installed in the circuit, to thereby realize the functions. Note that the processor is not limited to the case of being configured as a single processor circuit, but a plurality of independent circuits may be combined together to be configured as one processor to realize the functions. Further, the plurality of components in FIG. 1 may be integrated into one processor to realize the functions.

Next, one example of an imaging process of a long range image according to the present embodiment will be explained based on FIG. 2 and FIG. 3. FIG. 2 are schematic diagrams illustrating an imaging process of a long range image in a stepping method, and FIG. 3 are schematic diagrams illustrating an imaging process of long range imaging in an irradiation field division method. Both of FIG. 2 and FIG. 3 illustrate a case of performing imaging of a long range image by two times of imaging, by using a side view of the X-ray diagnostic apparatus 1.

Figure 2A:
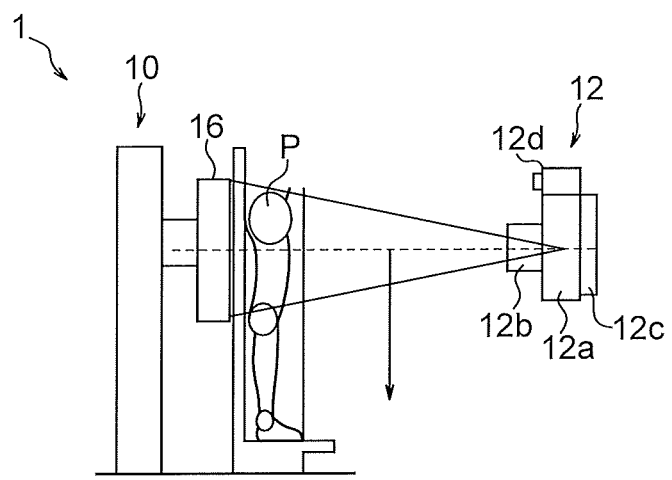
FIGS. 2A and 2B are schematic diagrams illustrating an imaging process of a long range image in a stepping method.
Figure 2B:
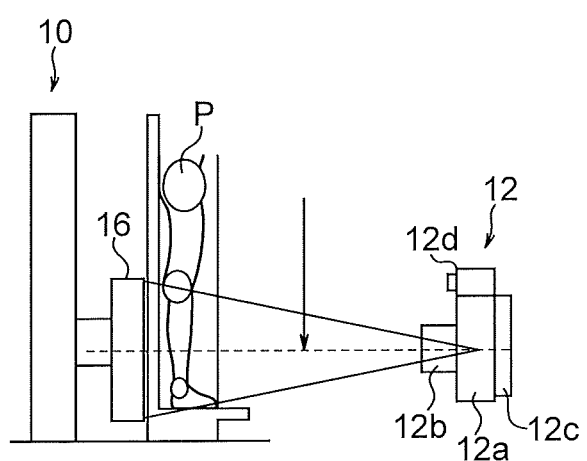

First, as illustrated in FIG. 2A, in the long range imaging in the stepping method, the X-ray tube holding device 12 and the X-ray detector 16 are moved to an upper position of an imaging target, and the imaging of the upper position of the imaging target of the subject P is carried out. Next, as illustrated in FIG. 2B, the X-ray tube holding device 12 and the X-ray detector 16 are moved to a lower position of the imaging target, and the imaging of the lower position of the imaging target of the subject P is carried out. In both of these two times of X-ray imaging, a center of the X-ray tube 12a of the X-ray tube holding device 12 and a center of the X-ray detector 16 coincide with each other, and the X-ray aperture 12b applies X-rays generated by the X-ray tube 12a toward a front direction.

Figure 3A:
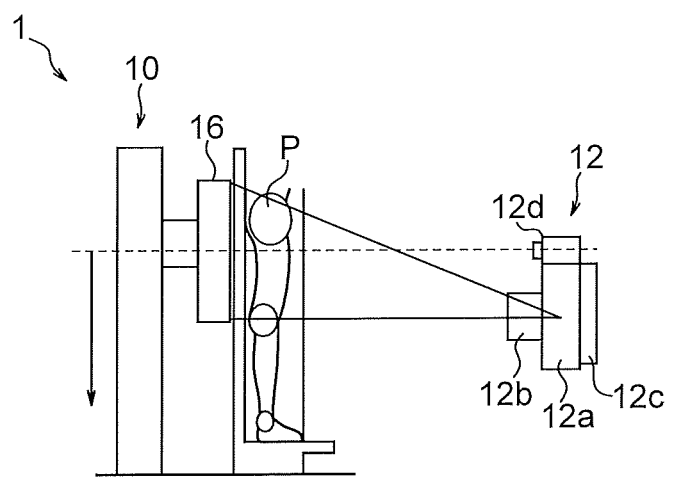
FIGS. 3A and 3B are schematic diagrams illustrating an imaging process of long range imaging in an irradiation field division method.
Figure 3B:
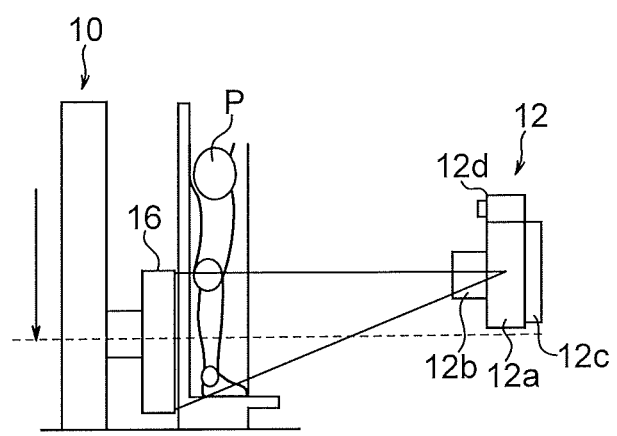

On the other hand, in the long range imaging in the irradiation field division method, the X-ray tube holding device 12 is fixed at a center position of the imaging target of the subject P, as illustrated in FIG. 3A. Subsequently, the X-ray detector 16 is moved to the upper position of the imaging target, and the imaging of the upper position of the imaging target of the subject P is carried out. Next, as illustrated in FIG. 3B, the X-ray detector 16 is moved to the lower position of the imaging target, and the imaging of the lower position of the imaging target of the subject P is carried out. In these two times of imaging, the position of the X-ray tube 12a of the X-ray tube holding device 12 does not move at the center position, so that the X-ray aperture 12b focuses X-rays on the upper position of the imaging target in the X-ray imaging of the first time, and focuses X-rays on the lower position of the imaging target in the X-ray imaging of the second time. Consequently, it is possible to perform the long range imaging only by moving the X-ray detector 16, without moving the X-ray tube holding device 12.

Figure 4:
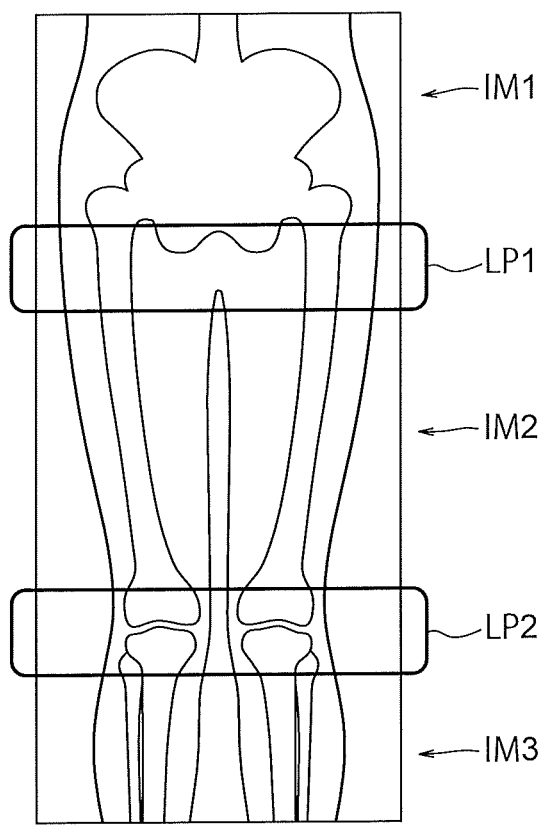
FIG. 4 is a diagram illustrating one example of an image obtained by generating one long range image through three times of X-ray imaging.

FIG. 4 is a diagram illustrating one example of an image obtained by generating one long range image through three times of X-ray imaging. If X-ray images IM1, IM2, IM3 are acquired at three different locations, and the images are synthesized to generate a long range X-ray image as above, it becomes necessary to perform blend processing on overlap regions LP1, LP2 of the different X-ray images IM1, IM2, IM3. Accordingly, the X-ray diagnostic apparatus 1 according to the present embodiment includes a function of preventing a region of interest and the like from being positioned at the overlap regions LP1, LP2, as will be described later. Specifically, each of the X-ray images IM1, IM2, IM3 indicates an irradiation range of X-rays when performing one time of imaging of an X-ray image.

Note that although FIG. 1 explains the example in which the X-ray diagnostic apparatus 1 performs the X-ray imaging on the standing subject P at the plural locations, and synthesizes these plural X-ray images to generate the long range X-ray image, it is also possible that the X-ray diagnostic apparatus 1 performs the X-ray imaging on the subject P in a dorsal position at plural locations, and synthesizes these plural X-ray images to generate a long range X-ray image.

Figure 5:
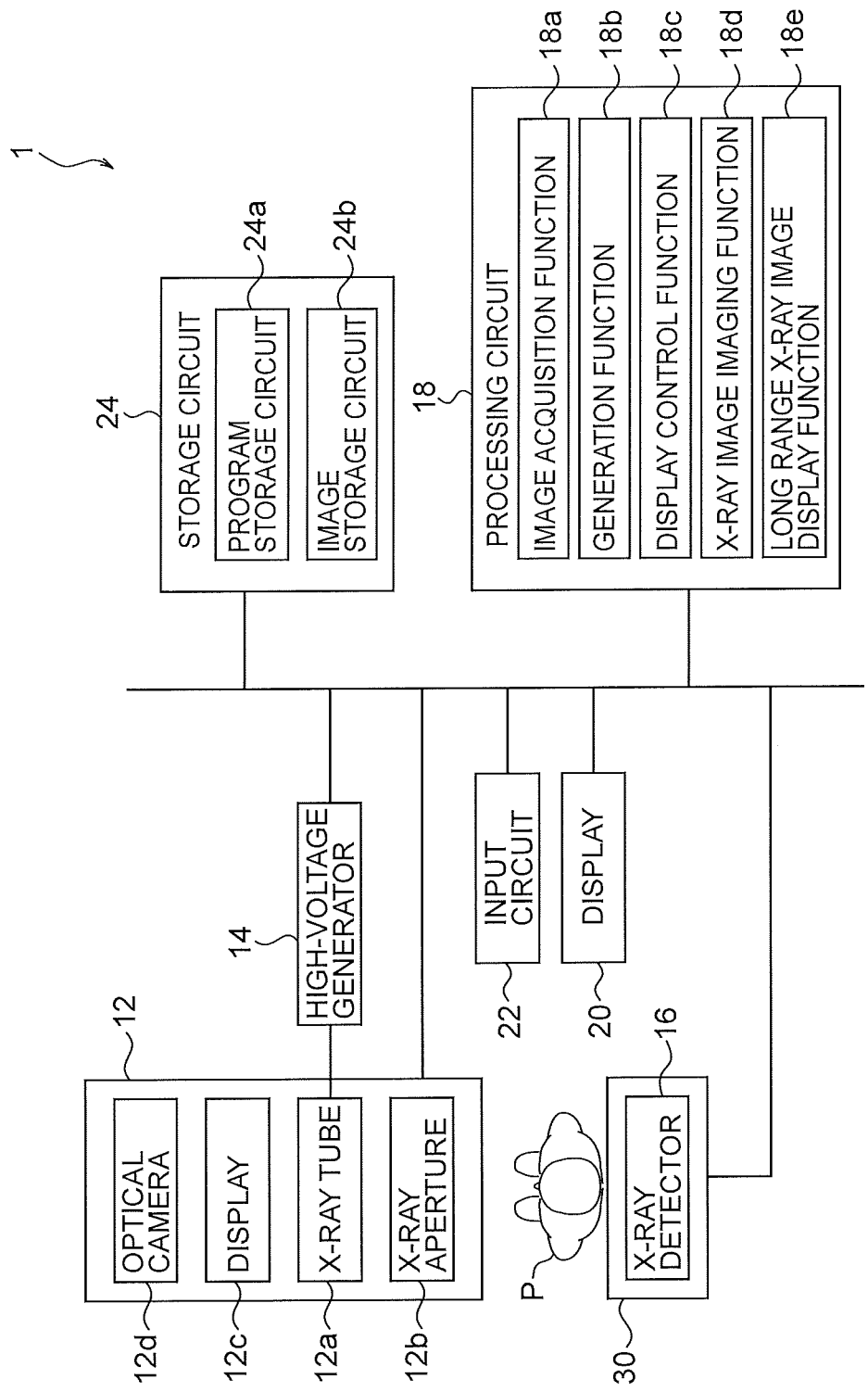
FIG. 5 is a block diagram explaining the entire configuration of the X-ray diagnostic apparatus according to the first embodiment (a case of dorsal position)

FIG. 5 is a block diagram explaining the entire configuration of the X-ray diagnostic apparatus 1 which performs X-ray imaging at plural different locations on the subject P in a dorsal position, and generates a long range X-ray image. As can be understood from FIG. 5, in the X-ray diagnostic apparatus 1 in FIG. 5, a bed 30 is provided instead of the stand 10 in the X-ray diagnostic apparatus 1 in FIG. 1. The subject P lies down on a top plate of the bed 30, and the X-ray imaging of the subject P in the dorsal position is carried out.

Specifically, the X-ray detector 16 is positioned under the bed 30, X-rays generated by the X-ray tube 12a of the X-ray tube holding device 12 are transmitted through the subject P on the bed 30, and the transmitted X-rays are detected by the X-ray detector 16. The configuration other than that in the X-ray diagnostic apparatus 1 in FIG. 5 is substantially the same as the configuration of the X-ray diagnostic apparatus 1 in FIG. 1.

Figure 6:
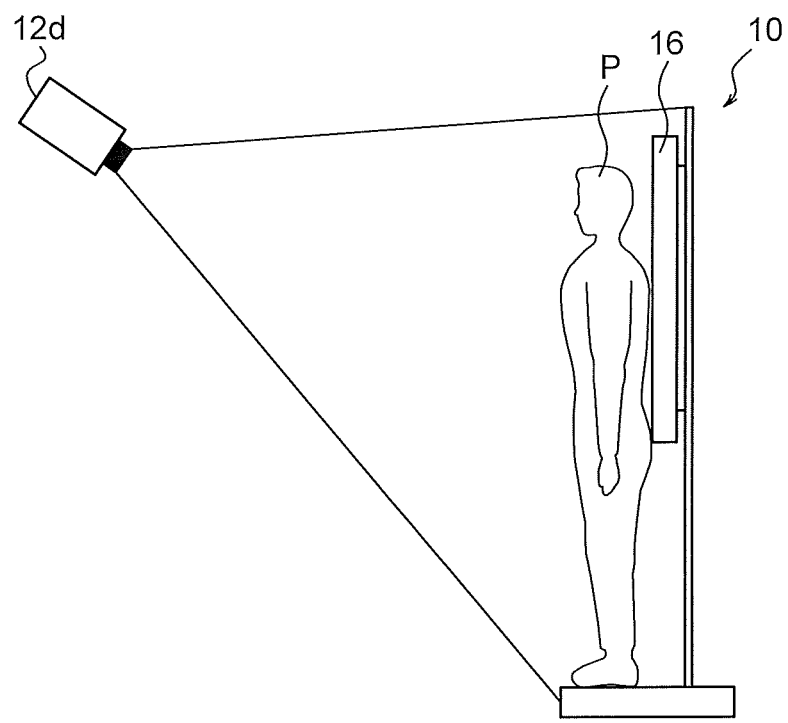
FIG. 6 is a diagram explaining an example of optical imaging performed by an optical camera in the X-ray diagnostic apparatus in FIG. 1.

FIG. 6 is a diagram explaining an example of optical imaging performed by the optical camera 12d in the X-ray diagnostic apparatus 1 in FIG. 1 described above. As illustrated in FIG. 6, the X-ray tube holding device 12 according to the present embodiment includes the wide-angle optical camera 12d, and with the use of this optical camera 12d, an image indicating the whole body of the standing subject P who is standing in front of the stand 10 can be optically imaged.

Figure 7:
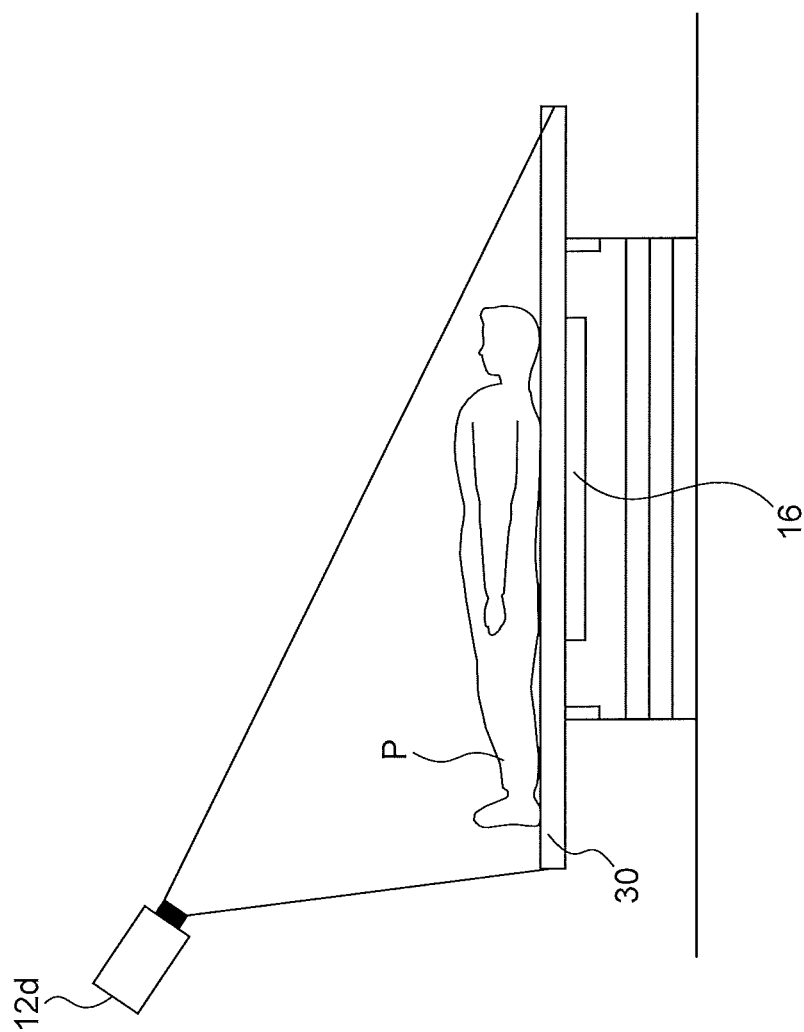
FIG. 7 is a diagram explaining an example of optical imaging performed by an optical camera in the X-ray diagnostic apparatus in FIG. 5.

FIG. 7 is a diagram explaining an example of optical imaging performed by the optical camera 12d in the X-ray diagnostic apparatus 1 in FIG. 5 described above. As illustrated in FIG. 7, the X-ray tube holding device 12 according to the present embodiment includes the wide-angle optical camera 12d, and with the use of this optical camera 12d, an image indicating the whole body of the subject P in a dorsal position who is lying down on the bed 30 can be optically imaged.

Next, long range image imaging processing which is executed in the X-ray diagnostic apparatus 1 according to the present embodiment will be explained based on FIG. 8. The long range image imaging processing illustrated in FIG. 8 is processing realized when the processing circuit 18 reads and executes a long range image imaging processing program stored in the program storage circuit 24a of the storage circuit 24.

Figure 8:
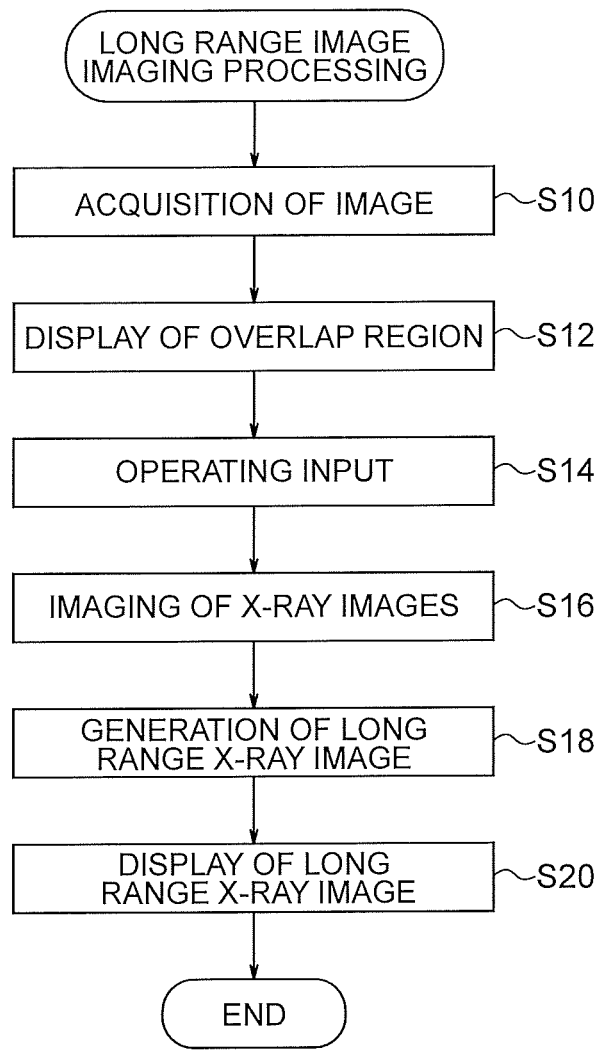
FIG. 8 is a diagram illustrating a flow chart that explains long range image imaging processing executed in the X-ray diagnostic apparatus in each of FIG. 1 and FIG. 5.

As illustrated in FIG. 8, the X-ray diagnostic apparatus 1 first acquires an image indicating the subject P (step S10). The processing of acquiring the image of the subject P is realized by the image acquisition function 18a of the processing circuit 18. In the present embodiment, for example, the optical camera 12d is used to perform optical imaging of the subject P, to thereby acquire the image of the subject P. The image of the subject P may be an image indicating the whole body of the subject P, or it may be an image indicating a part of the subject P.

Next, the X-ray diagnostic apparatus 1 generates an image including an overlap region where respective X-ray images are superimposed when performing imaging of X-ray images at plural different locations, on an image indicating the subject P, and displays the generated image as a preparation screen on the display 12c or the display 20 (step S12). In the present embodiment, the processing of generating the image including the overlap region and displaying the image as the preparation screen, is realized by the display control function 18c of the processing circuit 18.

Figure 9:
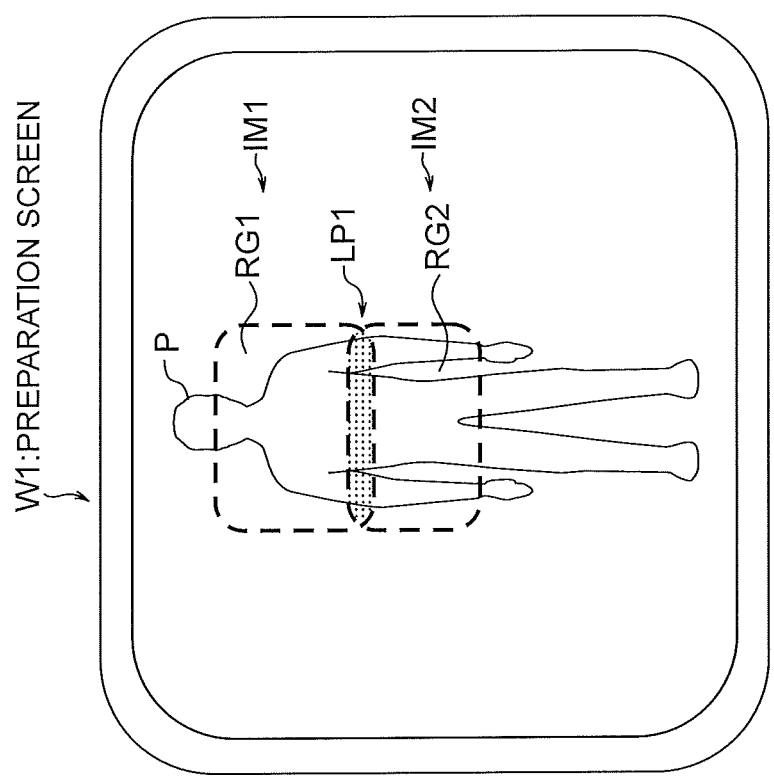
FIG. 9 is a diagram illustrating one example of a preparation screen which is displayed on a display of an X-ray diagnostic apparatus by step S12 of the long range image imaging processing.

FIG. 9 is a diagram illustrating one example of a preparation screen W1 which is displayed on the display 12c or the display 20 of the X-ray diagnostic apparatus 1 according to the present embodiment. As illustrated in FIG. 9, on the preparation screen W1, regions RG1, RG2 of X-ray images IM1, IM2 which are imaged at plural different positions are displayed in a virtual manner by being superimposed on the whole body image indicating the subject P acquired in step S10. The regions RG1, RG2 of the X-ray images IM1, IM2 indicate, in a virtual manner, regions which are imaged when performing imaging of X-ray images in step S16 to be described later. Specifically, each of the X-ray images IM1, IM2 indicates an irradiation range of X-rays in one time of X-ray imaging.

At a portion where the regions RG1, RG2 of the X-ray images IM1, IM2 are combined, there is formed an overlap region LP1 where both the images are superimposed. Specifically, FIG. 9 clearly expresses to an operator beforehand that when the long range imaging is performed with the setting indicated on the preparation screen W1 in FIG. 9, two X-ray images IM1, IM2 are generated by two times of X-ray imaging, and a long range image including the overlap region LP1 at a position indicated on the preparation screen W1 is generated. In other words, the overlap region LP1 indicates a region where an irradiation range of X-rays when performing imaging of the X-ray image IM1 and an irradiation range of X-rays when performing imaging of the X-ray image IM2 are overlapped. However, it can also be assumed that the overlap region LP1 is positioned at an unfavorable region such as a region of interest.

For this reason, in the X-ray diagnostic apparatus 1 according to the present embodiment, an operating input of moving the overlap region LP1 to change the position of the overlap region LP1 is subsequently accepted, as illustrated in FIG. 8 (step S14). In the present embodiment, the acceptance of the operating input is realized by the display 12c or the display 20 configured by a touch panel, under the control of the display control function 18c.

Figure 10:
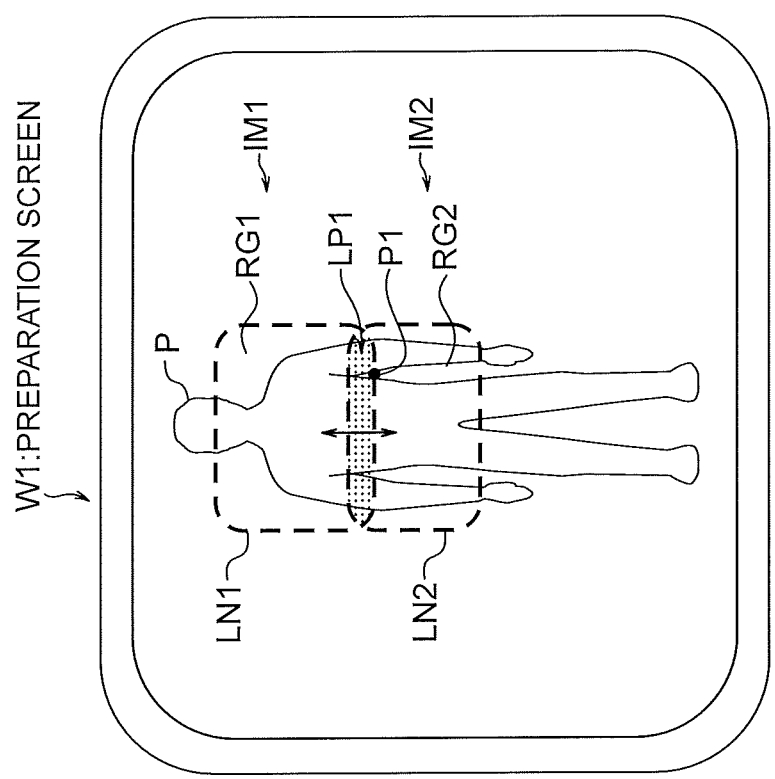
FIG. 10 is a diagram explaining one example of an operation of changing a position of an overlap region by using the preparation screen, the operation being performed by step S14 of the long range image imaging processing according to the first embodiment.

FIG. 10 is a diagram illustrating one example of the operating input of moving the overlap region LP1 to change the position of the overlap region LP1 on the preparation screen W1 according to the present embodiment. As illustrated in FIG. 10, in the present embodiment, the display 12c or the display 20 is configured by the touch panel, for example, so that the operator can change the position of the overlap region LP1 by performing a drag operation on the overlap region LP1 with his/her finger.

For example, when the overlap region LP1 is moved in the lower direction, the overlap region LP1 is dragged in the lower direction of the preparation screen W1 while being touched. This makes the overlap region LP1 move in the lower direction of the preparation screen W1. At this time, a size of the region RG1 of the X-ray image IM1 becomes large, and a size of the region RG2 becomes small. In this case, it is premised that the size of the overlap region LP1 is not changed.

On the contrary, when the overlap region LP1 is moved in the upper direction, the overlap region LP1 is dragged in the upper direction of the preparation screen W1 while being touched. This makes the overlap region LP1 move in the upper direction of the preparation screen W1. At this time, the size of the region RG2 of the X-ray image IM2 becomes large, and the size of the region RG1 becomes small. Also in this case, it is premised that the size of the overlap region LP1 is not changed.

Figure 11:
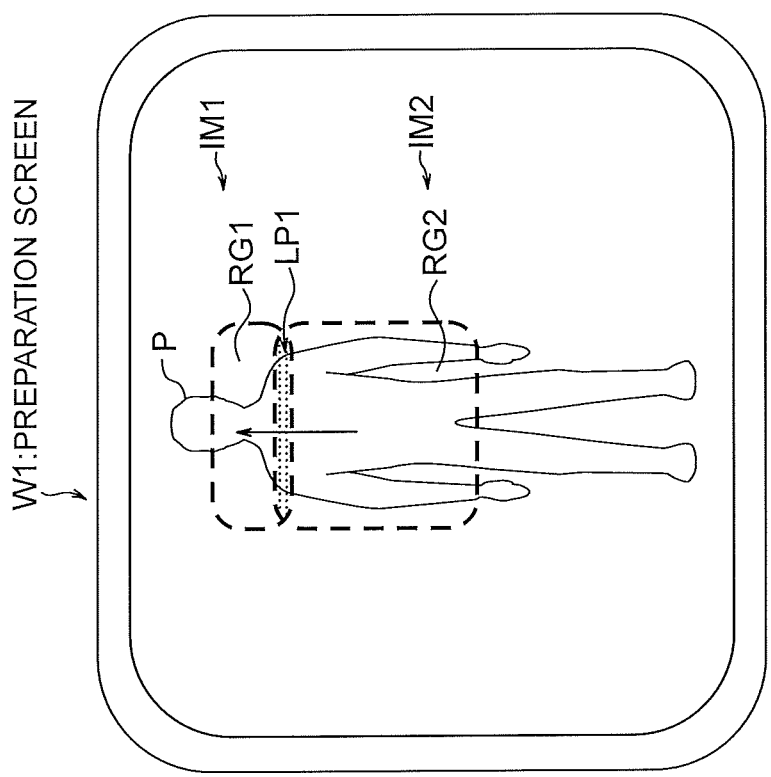
FIG. 11 is a diagram explaining another example of the operation of changing the position of the overlap region by using the preparation screen, the operation being performed by step S14 of the long range image imaging processing according to the first embodiment.

Note that in the example of FIG. 11, the size of the overlap region LP1 may be changed separately. For example, it is also possible to design such that when the operator performs long pressing of the overlap region LP1 displayed on the preparation screen W1 with his/her finger, the preparation screen W1 enters a size changing mode regarding the overlap region LP1, in which the size of the overlap region LP1 can also be changed when the operator moves lines LN1, LN2 of the X-ray images IM1, IM2. Further, at that time, it is also possible to limit the change of the size of the overlap region LP1 in order to prevent the overlap region LP1 between the X-ray image IM1 and the X-ray image IM2 from becoming small enough so that the combination processing or the blend processing cannot be performed.

Further, in the X-ray diagnostic apparatus 1 according to the present embodiment, it is configured to put limitations when, on the preparation screen W1 illustrated in FIG. 10 and FIG. 11, the operator tries to move the overlap region or the operator tries to increase the regions RG1, RG2 of the X-ray images IM1, IM2 in a manner of exceeding the maximum imaging range capable of being imaged by one time of X-ray imaging. Specifically, in the example of FIG. 10, it is configured such that when the size of the X-ray image IM1 is almost beyond the size capable of being imaged by one time, even if the operator tries to move the line LN1 of the X-ray image IM1, the line LN1 is not moved any more, for example. In the example of FIG. 11, it is configured such that when the size of the X-ray image IM1 is almost beyond the maximum imaging range capable of being imaged by one time, even if the operator tries to move the overlap region LP1, the overlap region LP1 is not moved any more, for example.

Next, as illustrated in FIG. 8, the X-ray diagnostic apparatus 1 performs imaging of X-ray images at plural different locations based on the setting made on the preparation screen W1 in step S14, and generates a long range X-ray image (step S16). Specifically, the X-ray imaging of the subject P is performed based on the plural X-ray imaging ranges having the overlap region set in step S14, and the long range X-ray image is generated. In the present embodiment, the generation of the long range X-ray image is realized by the X-ray image imaging function 18d of the processing circuit 18.

Figure 12:
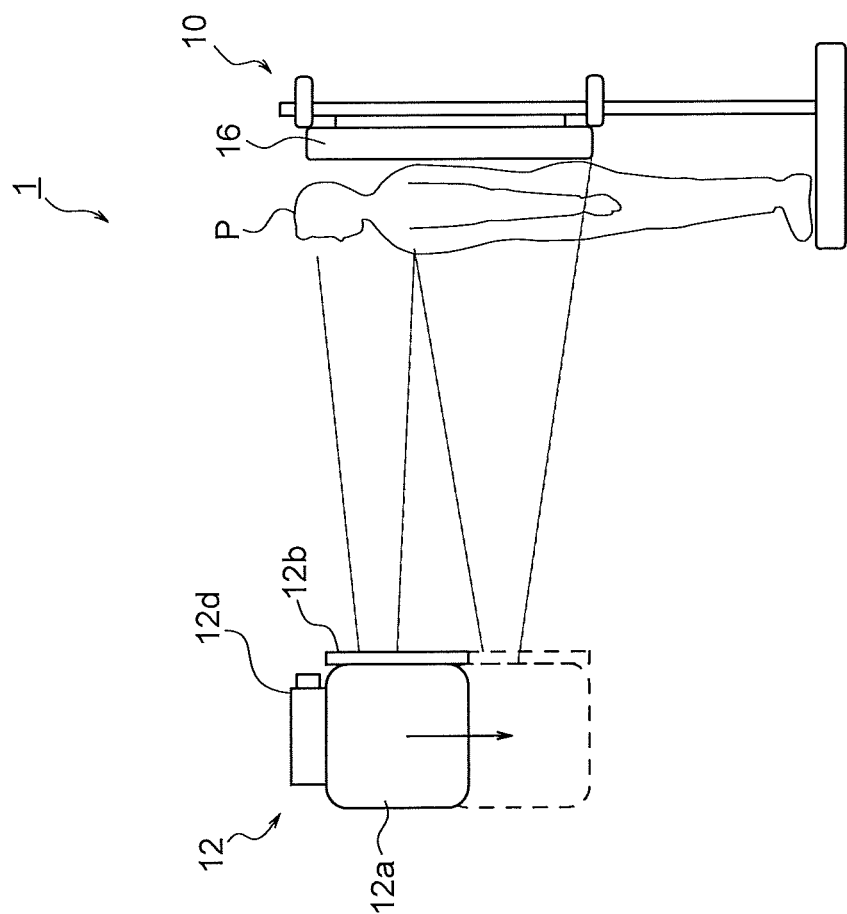
FIG. 12 is a diagram explaining a process of performing imaging of X-ray images at plural different locations for generating a long range X-ray image in the X-ray diagnostic apparatus.

FIG. 12 is a diagram explaining a process of performing imaging of X-ray images at plural different locations for generating a long range X-ray image in the X-ray diagnostic apparatus 1 according to the present embodiment. In the example illustrated in FIG. 12, imaging of an X-ray image of the first time is performed at an upper position of an imaging range with respect to the subject P, and subsequently, imaging of an X-ray image of the second time is performed at a lower position of the imaging range with respect to the subject P. An imaging region in the imaging of the first time may be small, so that in order to suppress an exposure dose of the subject P, the X-ray aperture 12b is narrowed to be small to perform the X-ray imaging. On the other hand, an imaging region is large in the imaging of the second time, so that the X-ray aperture 12b is widely opened to perform the X-ray imaging. As described above, the imaging of the plurality of X-ray images with different sizes and at different locations is performed based on the setting on the preparation screen W1.

Next, as illustrated in FIG. 8, the X-ray diagnostic apparatus 1 synthesizes the plurality of X-ray images imaged in step S16, to thereby generate a long range X-ray image (step S18). In the present embodiment, the generation of the long range X-ray image is realized by the generation function 18b of the processing circuit 18. Specifically, as illustrated in FIG. 4, since the X-ray images are imaged at the plural locations, these X-ray images are combined to be synthesized, thereby generating the long range X-ray image. At this time, the positions of the overlap regions LP1, LP2 are displaced from the region of interest and the like, so that it is possible to prevent the region of interest and the like from being influenced by the blend processing.

Next, as illustrated in FIG. 8, the X-ray diagnostic apparatus 1 displays the long range X-ray image generated in step S18 on the display 12c or the display 20 (step S20). The processing of displaying the long range X-ray image is realized by the long range X-ray image display function 18e of the processing circuit 18. Note that it is also possible to design such that the long range X-ray image generated in step S18 is housed to be stored in the image storage circuit 24b of the storage circuit 24 before or after it is displayed on the display 12c or the display 20.

As described above, according to the X-ray diagnostic apparatus 1 according to the present embodiment, it is designed such that before performing the imaging of the X-ray images for generating the long range X-ray image, it is possible to perform the adjustment and the change beforehand regarding that the overlap region LP1 is positioned on which part on the subject P, by using the preparation screen W1 displayed on the display 12c or the display 20. For this reason, it is possible to avoid a case that the overlap region LP1 is positioned at an unfavorable region such as a region of interest, which hinders correct diagnosis.

Specifically, in the overlap region LP1 of the plural X-ray images, there is a risk regarding a positional displacement caused by the performance of plural times of X-ray imaging. Accordingly, the positioning of the region of interest at the overlap region of the plural X-ray images should be avoided as much as possible, and with the use of the X-ray diagnostic apparatus 1 according to the present embodiment, this can be avoided by previously adjusting the position of the overlap region LP1.

Further, since it is designed such that the size of the X-ray image can be changed individually on the preparation screen W1, it is possible to change the position and the size of the overlap region LP1 in a flexible manner in accordance with the position of the region of interest and the like. Furthermore, it is designed such that the position of the overlap region LP1 can be changed by dragging the overlap region LP1 on the preparation screen W1 displayed on the display 12c or the display 20, so that the operability for the operator can be improved.

Note that the region of interest is only one example of a region where the overlap region LP1 is not favorable to be positioned. Specifically, it is possible to prevent the overlap region LP1 from being positioned at the region of interest, and not only that, the X-ray diagnostic apparatus 1 according to the present embodiment can exhibit an effect regarding every region where the overlap region LP1 is not favorable to be positioned. For example, when the overlap region LP1 is positioned at a sensitive region such as a reproductive organ of the subject P, this can be said as undesirable since the X-ray irradiation is performed two times. In such a case, in the X-ray diagnostic apparatus 1 according to the present embodiment, the operator can perform the change to prevent the overlap region LP1 from being positioned at the sensitive region, by using the preparation screen W1.

Second Embodiment

In the above-described first embodiment, it is limited such that when the size of each of the X-ray images IM1, IM2 is almost beyond the maximum imaging range capable of being imaged by one time on the preparation screen W1 displayed in step S14 of the long range image imaging processing, the X-ray images IM1, IM2 cannot be enlarged by exceeding the maximum imaging range in the operating input on the preparation screen W1. However, the second embodiment is designed such that, in such a case, the X-ray images are divided, for example, the two X-ray images IM1, IM2 are divided to be three X-ray images IM1, IM2, IM3. Hereinafter, a part different from that of the first embodiment will be described.

Figure 13:
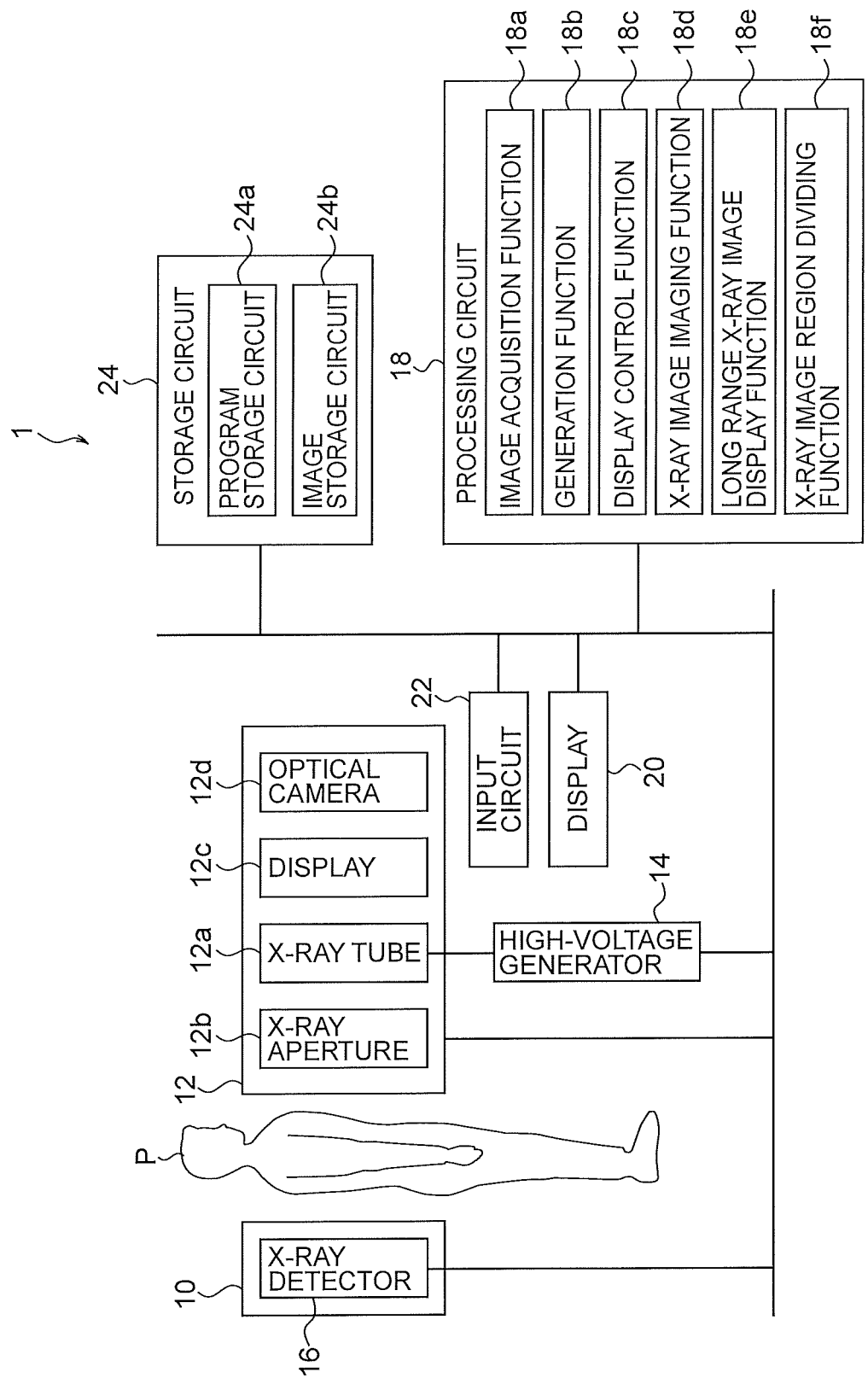
FIG. 13 is a block diagram explaining an entire configuration of an X-ray diagnostic apparatus according to a second embodiment (a case of standing position)

FIG. 13 is a block diagram explaining an entire configuration of the X-ray diagnostic apparatus 1 according to the present embodiment, and is a diagram corresponding to FIG. 1 described above. As illustrated in FIG. 13, the entire configuration of the X-ray diagnostic apparatus 1 according to the present embodiment is similar to that of the above-described first embodiment except that the processing circuit 18 additionally includes an X-ray image region dividing function 18f. This X-ray image region dividing function 18f is also a function which is realized when the processing circuit 18 reads and executes the program stored in the program storage circuit 24a of the storage circuit 24. This X-ray image region dividing function 18f corresponds to an X-ray image region divider in the present embodiment.

Figure 14:
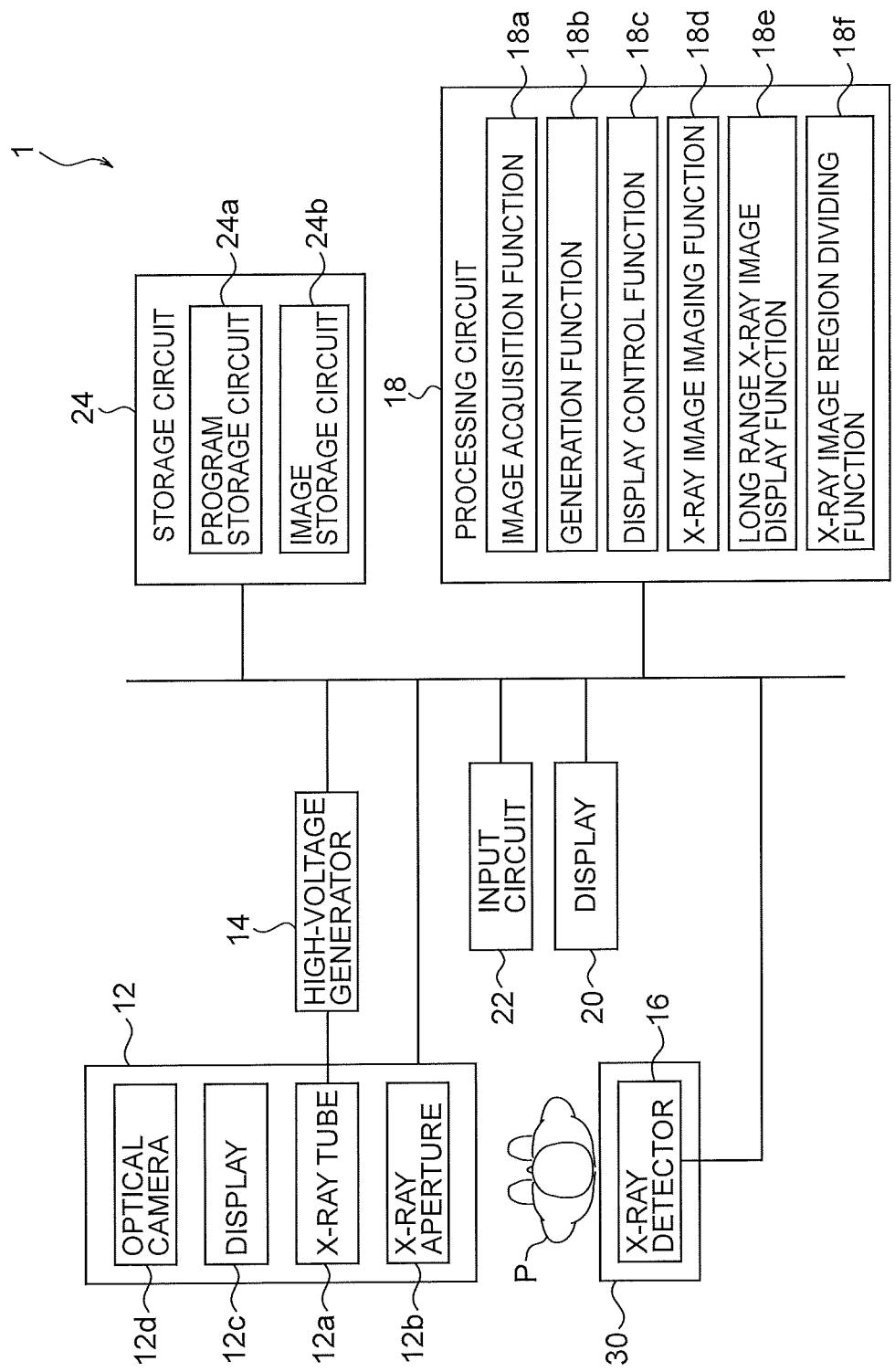
FIG. 14 is a block diagram explaining the entire configuration of the X-ray diagnostic apparatus according to the second embodiment (a case of dorsal position)

Note that when performing imaging of a long range X-ray image with respect to the subject P in a dorsal position, the present embodiment can be realized by additionally providing the X-ray image region dividing function 18f to the processing circuit 18 illustrated in FIG. 5, as illustrated in FIG. 14 which corresponds to FIG. 5 in the first embodiment.

Figures 15A, 15B:
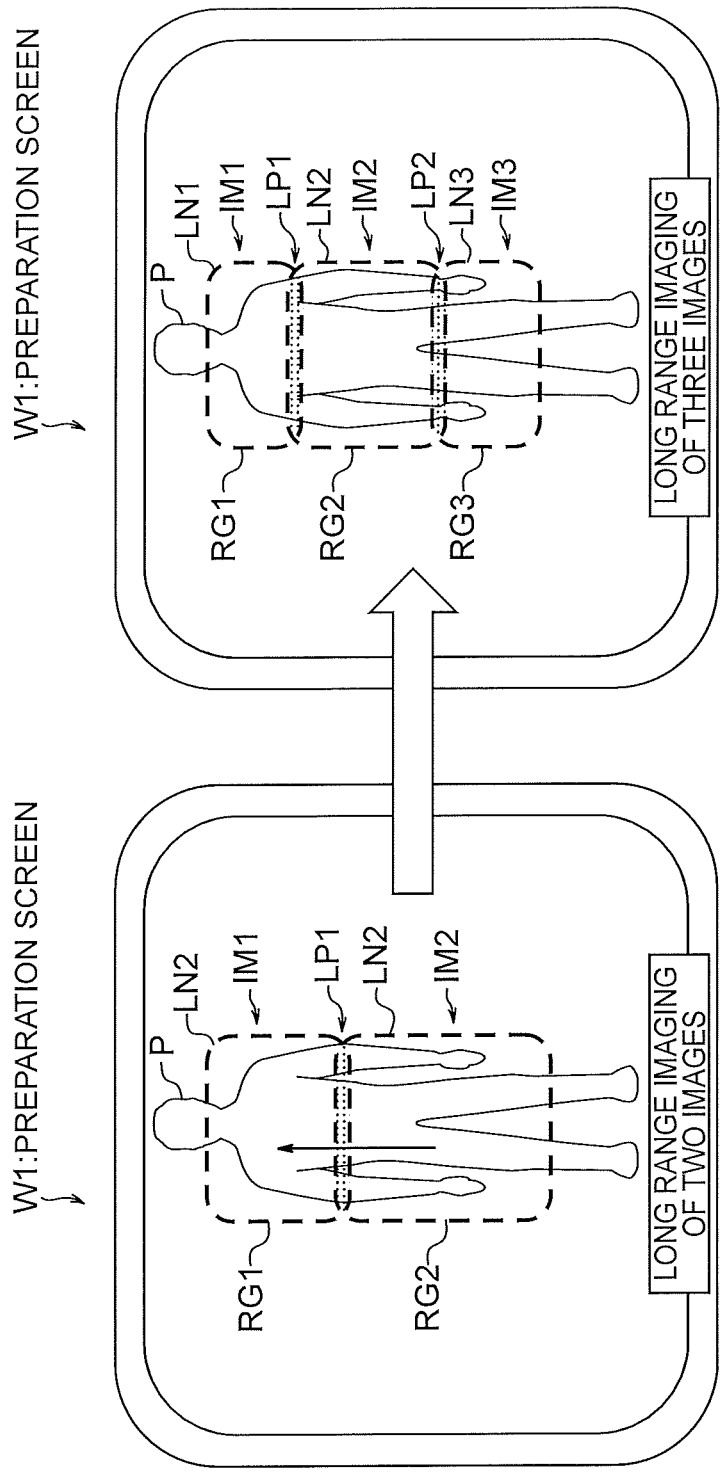
FIGS. 15A and 15B are diagrams explaining one example of an operation of changing a position of an overlap region by using a preparation screen, the operation being performed by step S14 of long range image imaging processing according to the second embodiment.

Although the X-ray diagnostic apparatus 1 illustrated in each of FIG. 13 and FIG. 14 executes the long range image imaging processing, similarly to FIG. 8 in the first embodiment described above, the operating input on the preparation screen W1 to be executed in step S14 of the processing is different. FIG. 15A and FIG. 15B are diagrams explaining the operating input on the preparation screen W1 displayed on the display 12c or the display 20 in step S14 of the long range image imaging processing.

As illustrated in FIG. 15A and FIG. 15B, in the present embodiment, when the region RG2 of the X-ray image IM2 exceeds the maximum imaging range as a result of moving the overlap region LP1 between the region RG1 of the X-ray image IM1 and the region RG2 of the X-ray image IM2 in the upper direction of the preparation screen W1, the region RG2 of the X-ray image IM2 is divided to generate an X-ray image IM3 having a region RG3. Specifically, when the region RG2 of the X-ray image IM2 exceeds a previously determined X-ray irradiation range being the maximum imaging range of the X-ray image IM2, it is set that the X-ray image IM2 is divided into two, and each of the divided and generated X-ray images IM2, IM3 falls within the X-ray irradiation range. Further, an overlap region LP2 is generated at a superimposed portion between the region RG2 of the X-ray image IM2 and the region RG3 of the X-ray image IM3. The division of the X-ray image IM2 is realized by the X-ray image region dividing function 18f of the processing circuit 18.

The division of the X-ray image IM2 may be automatically performed by the X-ray image region dividing function 18f, or the X-ray image region dividing function 18f may limit the change of the size once at a point where the region RG2 of the X-ray image IM2 exceeds the maximum imaging range, prompt the operator for confirmation through pop-up or the like, and then perform the division of the X-ray image IM2. The processing other than the above is similar to the processing of the above-described first embodiment.

As described above, according to the X-ray diagnostic apparatus 1 according to the present embodiment, it is designed such that when the X-ray image exceeds the maximum imaging range in the setting on the preparation screen W1, the X-ray image exceeding the maximum imaging range is divided. For this reason, the operator can easily move the overlap region LP1 to an arbitrary position of the subject P, without caring about the limitation of the maximum imaging range of the X-ray image.

Third Embodiment

In the above-described first embodiment and second embodiment, it is designed such that the operator moves the overlap region LP1 based on the preparation screen W1 displayed on the display 12c or the display 20. However, a third embodiment is designed such that when the overlap region LP1 is positioned at an avoidance region at which the overlap region LP1 is not desired to be positioned, the X-ray diagnostic apparatus 1 moves the overlap region LP1 to a position that avoids this avoidance region. Hereinafter, a part different from that of the above-described first embodiment and second embodiment will be described.

Figure 16:
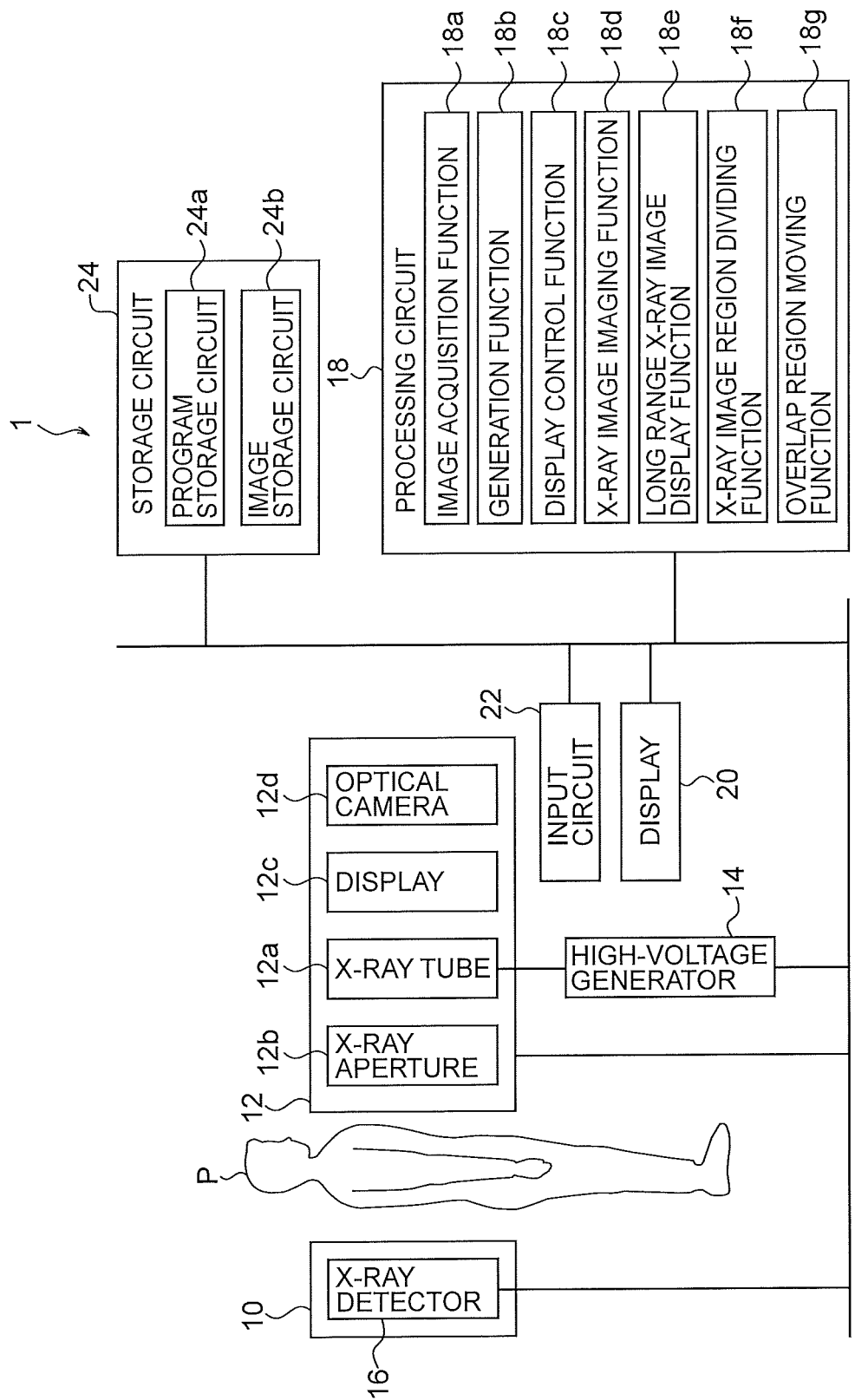
FIG. 16 is a block diagram explaining an entire configuration of an X-ray diagnostic apparatus according to a third embodiment (a case of standing position)

FIG. 16 is a block diagram explaining an entire configuration of the X-ray diagnostic apparatus 1 according to the third embodiment, and is a diagram corresponding to FIG. 1 described above. As illustrated in FIG. 16, the entire configuration of the X-ray diagnostic apparatus 1 according to the present embodiment is similar to that of the above-described first embodiment and second embodiment except that the processing circuit 18 additionally includes an overlap region moving function 18g. This overlap region moving function 18g is also a function which is realized when the processing circuit 18 reads and executes the program stored in the program storage circuit 24a of the storage circuit 24. This overlap region moving function 18g corresponds to a first overlap region mover and a second overlap region mover in the present embodiment.

Figure 17:
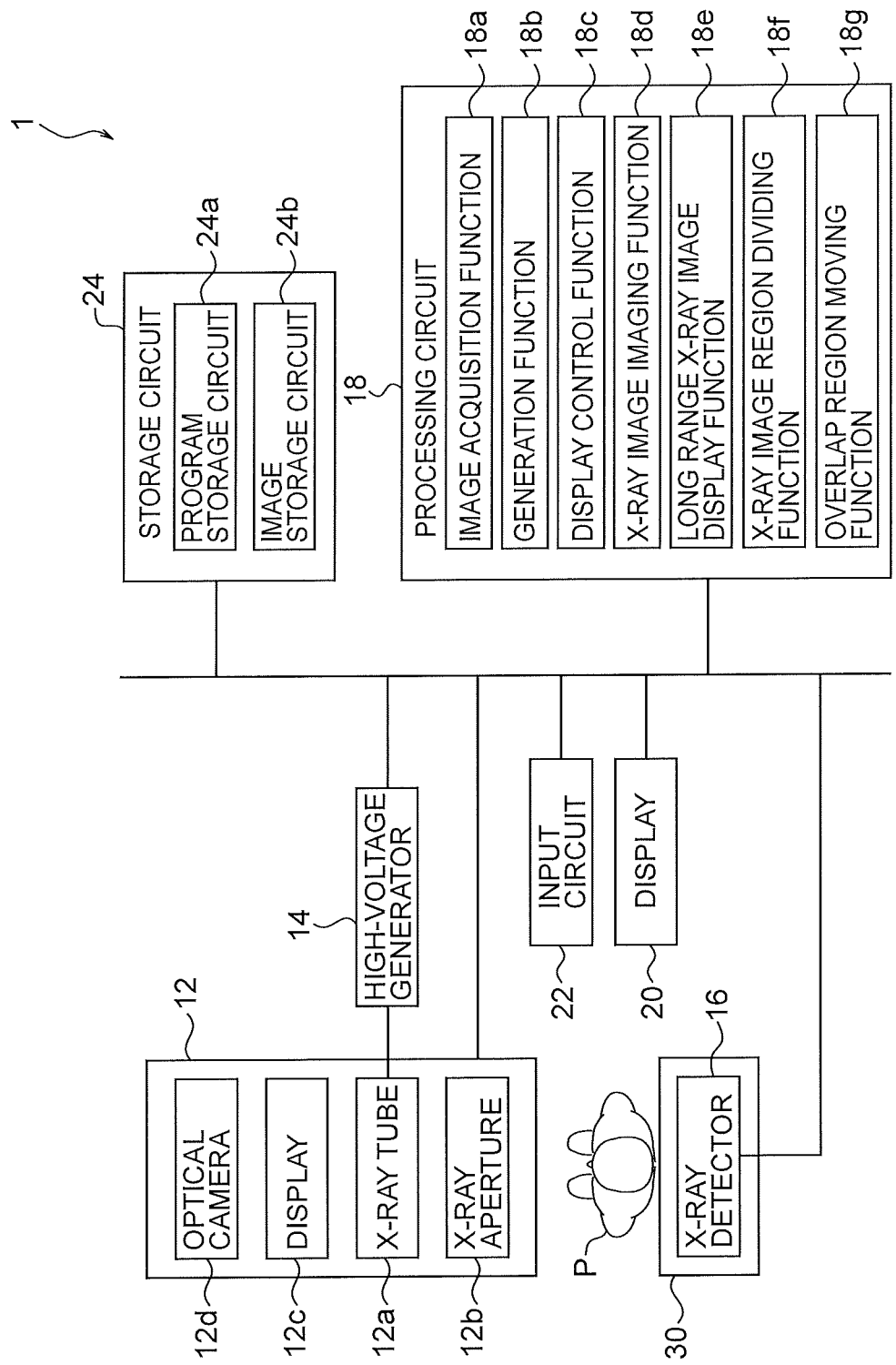
FIG. 17 is a block diagram explaining the entire configuration of the X-ray diagnostic apparatus according to the third embodiment (a case of dorsal position)

Note that when performing imaging of a long range X-ray image with respect to the subject P in a dorsal position, the present embodiment can be realized by additionally providing the overlap region moving function 18g to the processing circuit 18 illustrated in FIG. 5, as illustrated in FIG. 17 which corresponds to FIG. 5 in the first embodiment.

Figure 18:
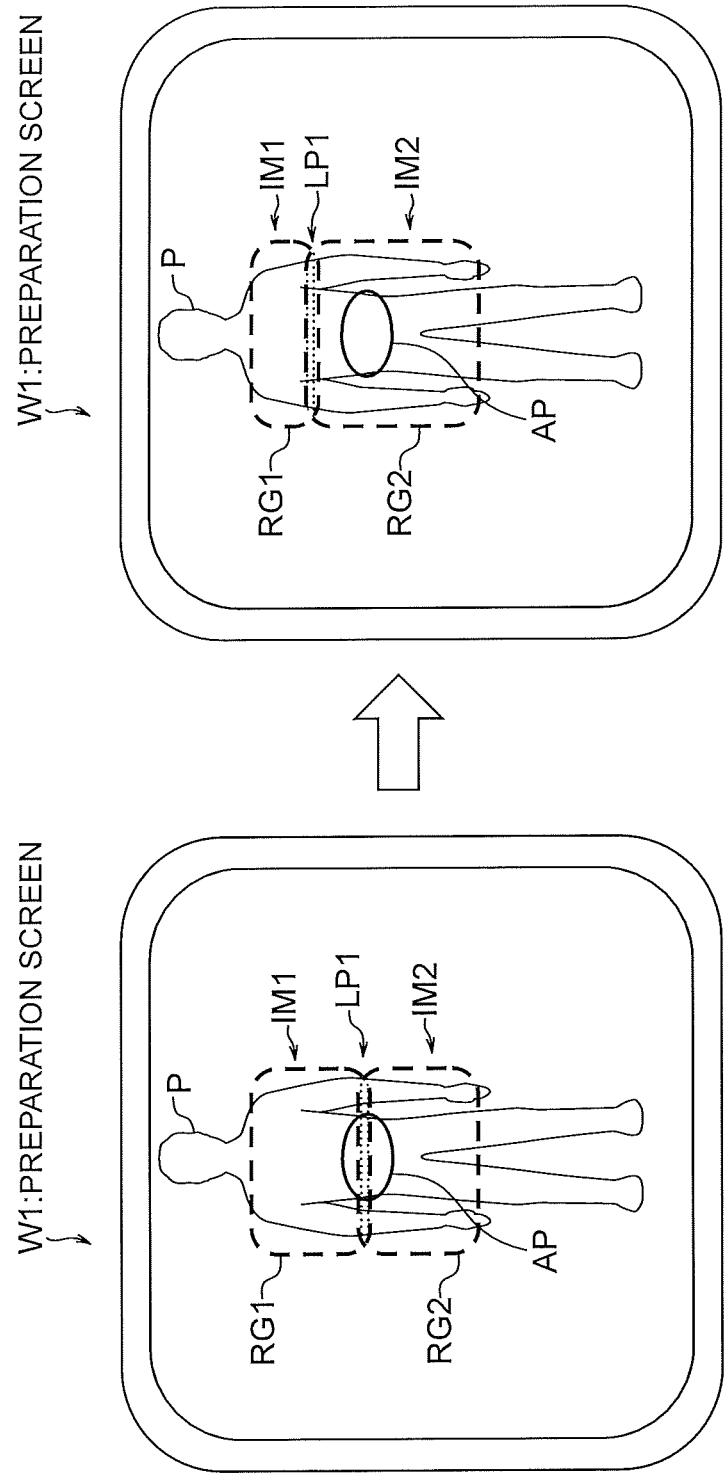
FIGS. 18A and 18B are diagrams explaining one example of an operation of changing a position of an overlap region by using a preparation screen, the operation being performed by step S14 of long range image imaging processing according to the third embodiment.

Although the X-ray diagnostic apparatus 1 illustrated in each of FIG. 16 and FIG. 17 executes the long range image imaging processing, similarly to FIG. 8 in the first embodiment described above, the operating input regarding the preparation screen W1 to be executed in step S14 of the processing is different. FIG. 18A and FIG. 18B are diagrams explaining the operating input regarding the preparation screen W1 displayed on the display 12c or the display 20 in step S14 of the long range image imaging processing.

As illustrated in FIG. 18A, in the example of the preparation screen W1, the overlap region LP1 between the X-ray image IM1 and the X-ray image IM2 is positioned at the region of interest of the subject P. For this reason, the operator touches, with his/her finger, the position of the region of interest of the subject P displayed on the display 12c or the display 20, to designate the position of the region of interest as an avoidance region AP. Consequently, the X-ray diagnostic apparatus 1 moves the overlap region LP1 to a position that avoids the avoidance region AP designated by the operator, as illustrated in FIG. 18B.

Concretely, the display control function 18c of the processing circuit 18 superimposes the region RG1 of the X-ray image IM1, the region RG2 of the X-ray image IM2, and the overlap region LP1 when performing the X-ray imaging in the initial setting state on the image of the subject P, and displays the superimposed image on the display 12c or the display 20 as the preparation screen W1. The operator who recognizes that the overlap region LP1 is positioned at the region of interest, designates the avoidance region AP at which the overlap region LP1 should be avoided, by touching the preparation screen W1 on the display 12c or the display 20, based on the image of the subject P.

When the avoidance region AP is designated, the overlap region moving function 18g of the processing circuit 18 compares the position of the designated avoidance region AP with the position of the overlap region LP1, and when the overlap region LP1 is positioned at the avoidance region AP, the overlap region moving function 18g moves the overlap region LP1 to a position which avoids the designated avoidance region AP. In the example of FIG. 18B, the region RG1 of the X-ray image IM1 is reduced and the region RG2 of the X-ray image IM2 is increased, thereby moving the overlap region LP1 in the upper direction of the preparation screen W1. Consequently, it is possible to move the overlap region LP1 to the position which avoids the designated avoidance region AP.

Although the example of moving the overlap region LP1 is arbitrary, it is also possible to design such that, for example, an X-ray image having the smallest region among a plurality of existing X-ray images is enlarged to be moved, or an X-ray image having the largest region is reduced to be moved. Further, it is also possible to design such that an X-ray image for enlarging or reducing its region is randomly selected to be moved.

It is also possible to assume a case that, as a result of enlarging the X-ray image, the region of the X-ray image exceeds the maximum imaging range. When the present embodiment is applied to the first embodiment, the operator is notified that the X-ray image exceeds the maximum imaging range, and a setting to increase the number of X-ray images to be imaged by the operator is performed with respect to the X-ray diagnostic apparatus 1. When the present embodiment is applied to the second embodiment, there is performed processing in which the X-ray image region dividing function 18f divides the region of the X-ray image which exceeds the maximum imaging range to increase the number of images to be imaged.

As described above, according to the X-ray diagnostic apparatus 1 according to the present embodiment, it is designed such that, based on the image of the subject P displayed by the display control function 18c, the operator can designate the avoidance region AP where the overlap region is avoided from being positioned, on the display 12c or the display 20, so that the overlap region can be moved more easily. Specifically, the operator can move the overlap region to the position that avoids the avoidance region AP, only by designating the avoidance region AP by touching the display 12c or the display 20.

Note that in the example of FIG. 18A and FIG. 18B described above, it is designed such that the operator designates the avoidance region AP after the subject P and the regions RG1, RG2 of the X-ray images IM1, IM2 are displayed on the preparation screen W1 of the display 12c or the display 20, but, this avoidance region AP can also be set previously.

Figure 19:
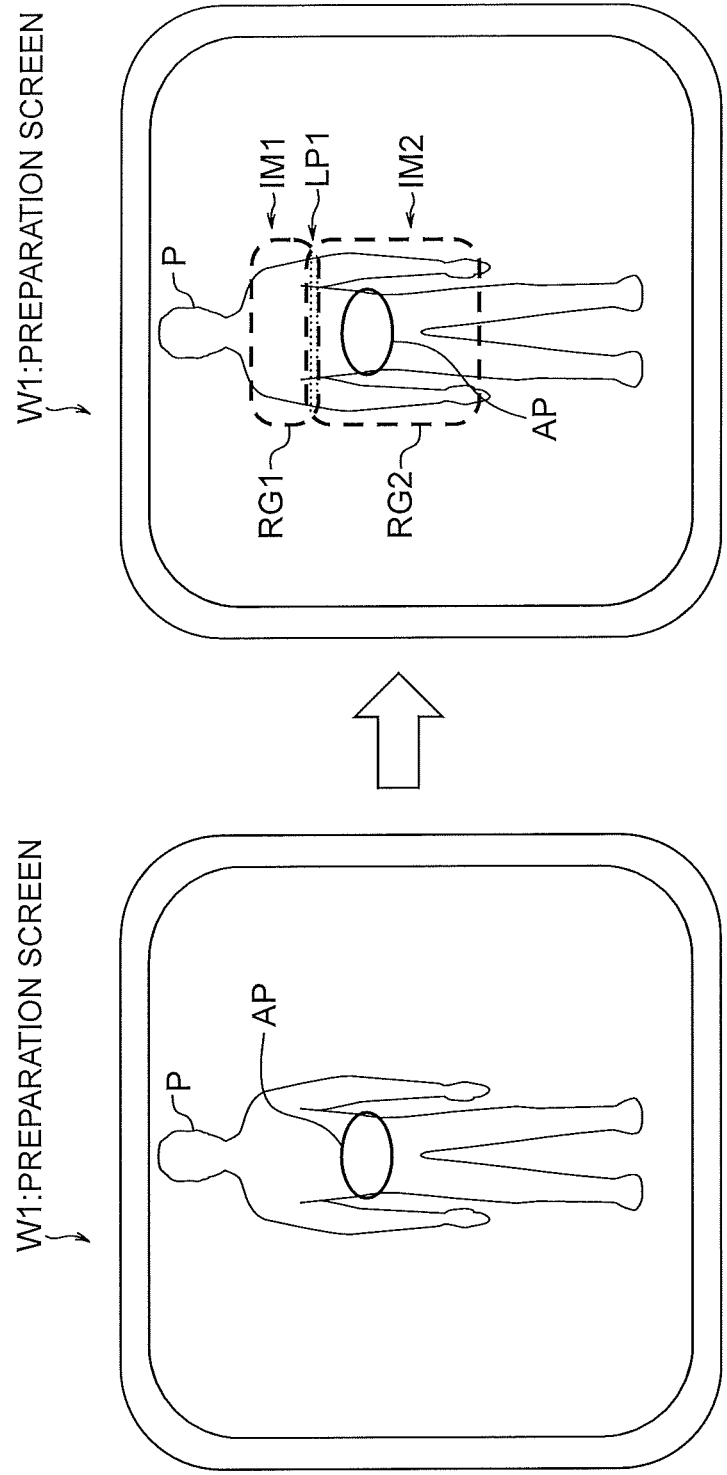
FIGS. 19A and 19B are diagrams explaining another example of the operation of changing the position of the overlap region by using the preparation screen, the operation being performed by step S14 of the long range image imaging processing according to the third embodiment.

For example, as illustrated in FIG. 19A, when the preparation screen W1 is displayed in step S14, the subject P is displayed but the regions RG1, RG2 of the X-ray images IM1, IM2 are not displayed yet. In this state, the operator touches the display 12c or the display 20 to previously set the avoidance region AP where the overlap region LP1 should be avoided from being positioned.

When the avoidance region AP is set, the overlap region moving function 18g of the processing circuit 18 compares the position of the set avoidance region AP with the position of the overlap region LP1 to be displayed, and when the overlap region LP1 is positioned at the avoidance region AP, the overlap region moving function 18g moves the overlap region LP1 to a position which avoids the set avoidance region AP, and then displays the regions RG1, RG2 of the X-ray images IM1, IM2 on the preparation screen W1. In an example of FIG. 19B, in a state where the region RG1 of the X-ray image IM1 is reduced and the region RG2 of the X-ray image IM2 is increased, the overlap region LP1 is formed, and the regions RG1, RG2 of the X-ray images IM1, IM2 are displayed. Also in such an example, it is possible to move the overlap region LP1 to the position which avoids the avoidance region AP. Accordingly, the display 12c or the display 20 configured by the touch panel corresponds to an avoidance designator and an avoidance setter in the present embodiment.

Fourth Embodiment

In the respective embodiments described above, the optical camera 12d is provided to the X-ray tube holding device 12, but, this optical camera 12d can also be omitted. In the fourth embodiment, a modified example of the X-ray diagnostic apparatus 1 which omits this optical camera 12d will be described. Hereinafter, a part different from that of the above-described first embodiment will be described.

Figure 21:
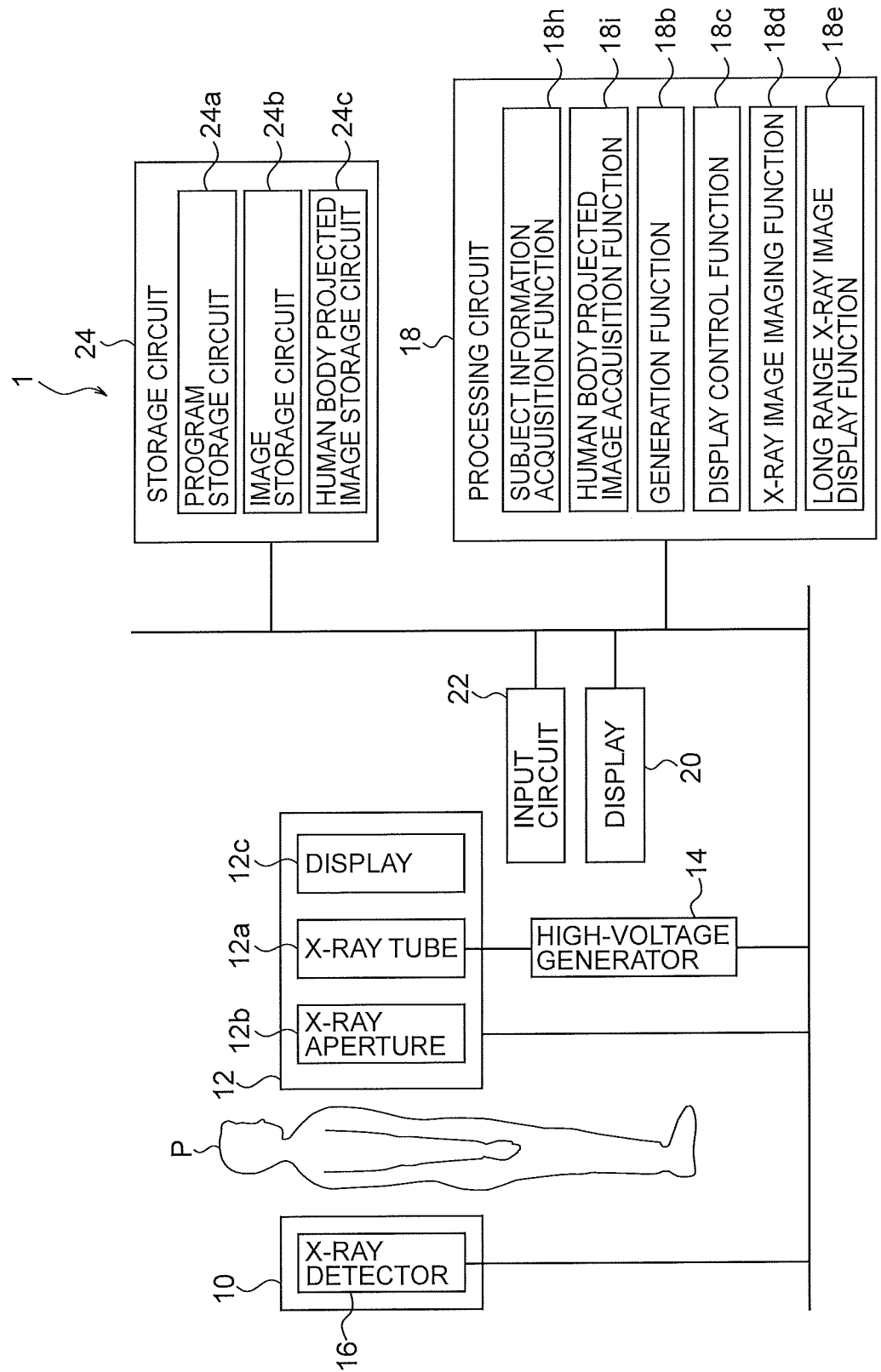
FIG. 21 is a block diagram explaining an entire configuration of an X-ray diagnostic apparatus according to a fourth embodiment (a case of standing position)

FIG. 21 is a block diagram explaining an entire configuration of the X-ray diagnostic apparatus 1 according to the fourth embodiment. As illustrated in FIG. 21, in the X-ray diagnostic apparatus 1 according to the present embodiment, the optical camera 12d is not provided to the X-ray tube holding device 12. However, it is possible to realize the present embodiment to be described below also in the X-ray diagnostic apparatus 1 in which the optical camera 12d is provided to the X-ray tube holding device 12.

Further, in the present embodiment, the configuration of the processing circuit 18 and the storage circuit 24 is different from that of the above-described first embodiment. Specifically, in the processing circuit 18, a subject information acquisition function 18h and a human body projected image acquisition function 18i are provided in place of the image acquisition function 18a. Further, in the storage circuit 24, a human body projected image storage circuit 24c is additionally provided.

Figure 22:
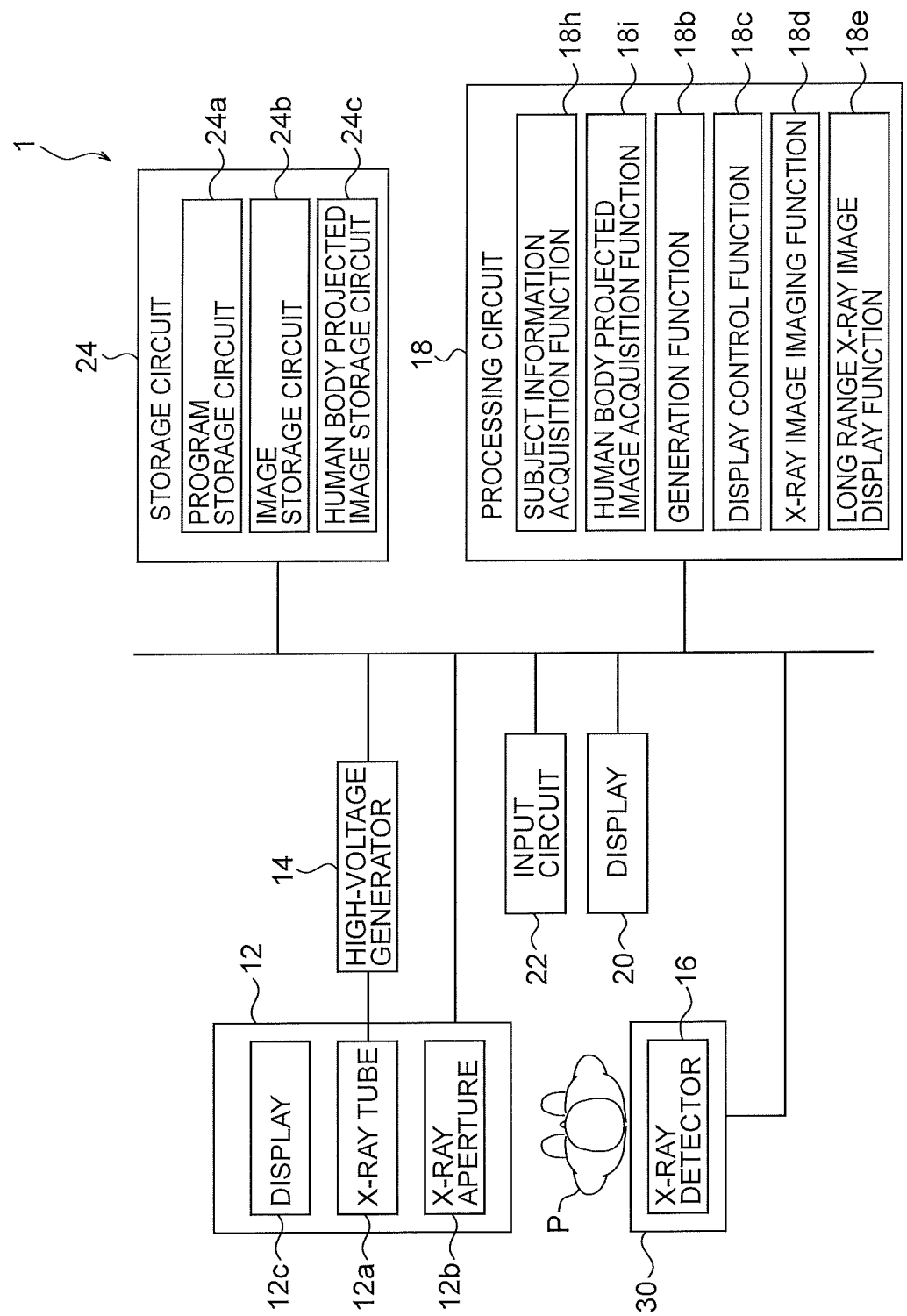
FIG. 22 is a block diagram explaining the entire configuration of the X-ray diagnostic apparatus according to the fourth embodiment (a case of dorsal position)

FIG. 21 is a block diagram of the X-ray diagnostic apparatus 1 in which a standing subject P is subjected to X-ray imaging, and a long range X-ray image is generated, but, it is also possible to design such that the subject P in a dorsal position is subjected to X-ray imaging, and a long range X-ray image is generated, similarly to the above-described first embodiment. FIG. 22 is a block diagram explaining an entire configuration of the X-ray diagnostic apparatus 1 in which the subject P in a dorsal position is subjected to X-ray imaging at plural different locations, and a long range X-ray image is generated. As can be understood from FIG. 22, in the present embodiment, the optical camera 12d of the X-ray tube holding device 12 is omitted also in the X-ray diagnostic apparatus 1 which performs the X-ray imaging of the subject P in a dorsal position.

Figure 23:
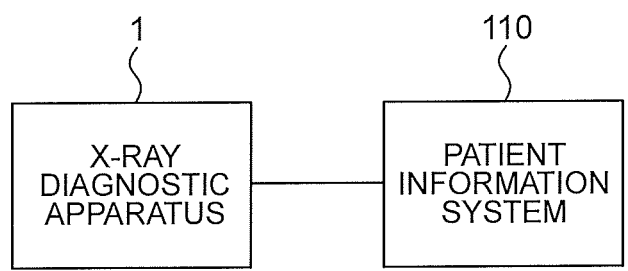
FIG. 23 is a block diagram illustrating the X-ray diagnostic apparatus and a patient information system connected to the X-ray diagnostic apparatus.

The X-ray diagnostic apparatus 1 illustrated in each of FIG. 21 and FIG. 22 is connected to a patient information system 110 in a communicable manner, as illustrated in FIG. 23. The patient information system 110 is, for example, a system that manages information regarding individual patients such as an electronic medical chart and a medication history, and in the present embodiment, information such as age, stature, weight, sex, and race of patients, in particular, is stored. Further, in the present embodiment, the patient information system 110 may also store, in addition to these or in place of these, information regarding whether a patient is an adult or a child.

Figure 24:
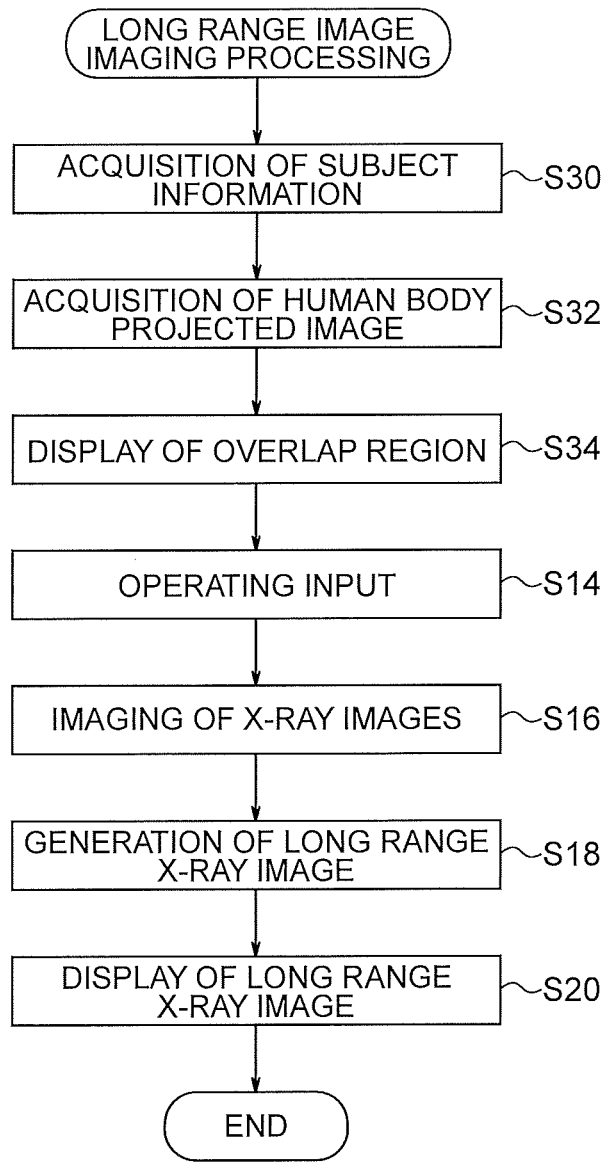
FIG. 24 is a diagram illustrating a flow chart that explains long range image imaging processing executed by the X-ray diagnostic apparatus in each of FIG. 22 and FIG. 23.

Next, long range image imaging processing which is executed by the X-ray diagnostic apparatus 1 according to the present embodiment will be described based on FIG. 24. The long range image imaging processing illustrated in FIG. 24 is processing which is realized when the processing circuit 18 reads and executes a long range image imaging processing program stored in the program storage circuit 24*a* of the storage circuit 24. Further, the long range image imaging processing illustrated in FIG. 24 is processing corresponding to the long range image imaging processing illustrated in FIG. 8 in the above-described first embodiment.

As illustrated in FIG. 24, the X-ray diagnostic apparatus 1 first acquires information regarding the subject P (step S30). The information regarding the subject P is acquired by the X-ray diagnostic apparatus 1 in a manner that the X-ray diagnostic apparatus 1 searches for information regarding the corresponding subject P from the information regarding patients stored in the patient information system 110. In the present embodiment, the X-ray diagnostic apparatus 1 acquires the stature of the subject P, for example. Note that in the present embodiment, the processing of acquiring the information regarding the subject P is realized by the subject information acquisition function 18*h* of the processing circuit 18.

Next, the X-ray diagnostic apparatus 1 generates and acquires a human body projected image based on the acquired information regarding the subject P (step S32). In the present embodiment, the stature is acquired as the information regarding the subject P, so that a human body projected image is generated and acquired based on the stature. For example, when the stature of the subject P is high to be 180 cm, a human body projected image based on the high stature of 180 cm is generated. On the other hand, when the stature of the subject P is low to be 150 cm, a human body projected image based on the low stature of 150 cm is generated.

In the present embodiment, the processing of generating and acquiring the human body projected image is realized by the human body projected image acquisition function 18*i* of the processing circuit 18. Specifically, the human body projected image acquisition function 18*i* of the processing circuit 18 reads data of the most appropriate human body projected image from the human body projected image storage circuit 24*c* of the storage circuit 24 and generates the human body projected image based on the information regarding the subject P. For this reason, the human body projected image storage circuit 24*c* stores data of a plurality of human body projected images, for example, and the human body projected image acquisition function 18*i* acquires data of the most approximated human body projected image based on the information of the subject P. In the example of the present embodiment, the human body projected image storage circuit 24*c* stores data of human body projected images regarding the stature from 130 cm to 200 cm in increments of 10 cm. Further, the human body projected image acquisition function 18*i* acquires data of the human body projected image with the most approximated stature from the human body projected image storage circuit 24*c*, based on the information regarding the stature of the subject P.

At that time, the human body projected image acquisition function 18*i* may generate a human body projected image by appropriately correcting the read data of the human body projected image based on the information regarding the subject P. For example, it is also possible that when the stature of the subject P is 165 cm, data of a human body projected image of 160 cm and data of a human body projected image of 170 cm are both acquired, and data of a human body projected image in the middle of both the images is generated. Consequently, it is possible to acquire a human body projected image with higher precision.

Note that the information regarding the subject P is not limited to the stature. For example, it is also possible to design such that a somatotype is analogized based on the stature and the weight of the subject P, and a human body projected image on which the analogized somatotype is also reflected is generated. Further, it is also possible to design such that the sex of the subject P is acquired, and a human body projected image of male is generated when the subject P is male, and a human body projected image of female is generated when the subject P is female. In each of the above cases, data of the human body projected image according to the somatotype of the subject P or according to the sex of the subject P is stored in the human body projected image storage circuit 24*c*.

In addition, it is also possible to generate a human body projected image based on the information regarding whether the subject P is an adult or a child, in place of the stature of the subject P. Specifically, when the subject P is an adult, a human body projected image suggestive of an adult may be generated, and when the subject P is a child, a human body projected image suggestive of a child may be generated. In this case, data of the adult human body projected image and data of the child human body projected image are stored in the human body projected image storage circuit 24*c*. Consequently, although the precision of the human body projected image becomes coarse, it is possible to reduce an amount of information in the human body projected image storage circuit 24*c*.

Alternatively, it is also possible to design such that a human body projected image which is generated when the subject P is a child is only made to be smaller than a human body projected image which is generated when the subject P is an adult. In this case, it becomes unnecessary to store data of a child human body projected image in the human body projected image storage circuit 24*c*, and thus it is possible to further reduce an amount of information stored in the human body projected image storage circuit 24*c*.

Further, it is also possible to design such that a human body projected image to be generated is generated based on the race of the subject P. For example, when the race is the Occidental race, a human body projected image with long legs may be generated, or when the race is the Oriental race, a human body projected image with short legs may be generated. In this case, data of human body projected images according to the races is stored in the human body projected image storage circuit 24*c*.

Note that in the present embodiment, it is set that the X-ray diagnostic apparatus 1 acquires the information regarding the subject P from the patient information system 110, but, the X-ray diagnostic apparatus 1 can acquire the information regarding the subject P through various methods. For example, before starting the X-ray imaging, the operator of the X-ray diagnostic apparatus 1 may manually input the stature, the weight, and so on of the subject P into the X-ray diagnostic apparatus 1 from the input circuit 22.

Next, the X-ray diagnostic apparatus 1 generates an image including an overlap region where respective X-ray images are superimposed when performing imaging of X-ray images at plural different locations, on an image of the acquired human body projected image indicating the subject P, and displays the generated image on the display 12c or the display 20 as the preparation screen (step S34). In the present embodiment, the processing of generating the image including the overlap region and displaying the image as the preparation screen, is realized by the display control function 18c of the processing circuit 18.

Figure 25:
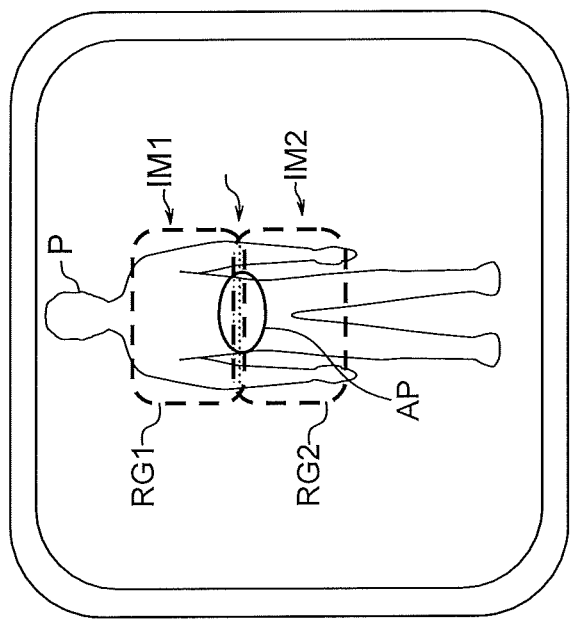
FIG. 25 is a diagram illustrating one example of a preparation screen which is displayed on a display of the X-ray diagnostic apparatus by step S34 of the long range image imaging processing.

FIG. 25 is a diagram illustrating one example of the preparation screen W1 which is displayed on the display 12c or the display 20 of the X-ray diagnostic apparatus 1 according to the present embodiment. As illustrated in FIG. 25, on the preparation screen W1, the regions RG1, RG2 of the X-ray images IM1, IM2 which are imaged at plural different positions are displayed in a virtual manner by being superimposed on the human body projected image indicating the subject P acquired in step S32. The regions RG1, RG2 of the X-ray images IM1, IM2 indicate, in a virtual manner, regions which are imaged when performing imaging of X-ray images in step S16.

Next, the X-ray diagnostic apparatus 1 accepts an operating input for changing the position of the overlap region LP1 in step S14. Note that the processing of step S14 and thereafter is similar to that of the above-described first embodiment, so that detailed explanation thereof will be omitted.

As described above, according to the X-ray diagnostic apparatus 1 according to the present embodiment, it is designed such that the human body projected image is generated and acquired based on, not the imaging of the subject P using the optical camera 12d but the information regarding the subject P acquired from the patient information system 110, and the preparation screen W1 is displayed by using the human body projected image. For this reason, it is possible to realize the X-ray diagnostic apparatus 1 according to the first embodiment without using the optical camera 12d.

Note that in the above description, the case of applying the modified example which does not require the mounting of the optical camera 12d to the X-ray diagnostic apparatus 1 according to the first embodiment has been described as the fourth embodiment, but, the modified example which does not require the mounting of the optical camera 12d can also be applied to the X-ray diagnostic apparatuses 1 according to the second embodiment and the third embodiment.

Fifth Embodiment

Although the above-described fourth embodiment is designed such that the operator of the X-ray diagnostic apparatus 1 uses the preparation screen W1 to set the overlap region LP1 so as to avoid the avoidance region AP being the region of interest, in a fifth embodiment, it is designed such that the overlap region LP1 is set in a manner of avoiding the avoidance region AP being the region of interest by using examination information of the subject P, even if the operator does not perform the setting using the preparation screen W1. Hereinafter, a part different from that of the above-described fourth embodiment will be described.

Figure 26:
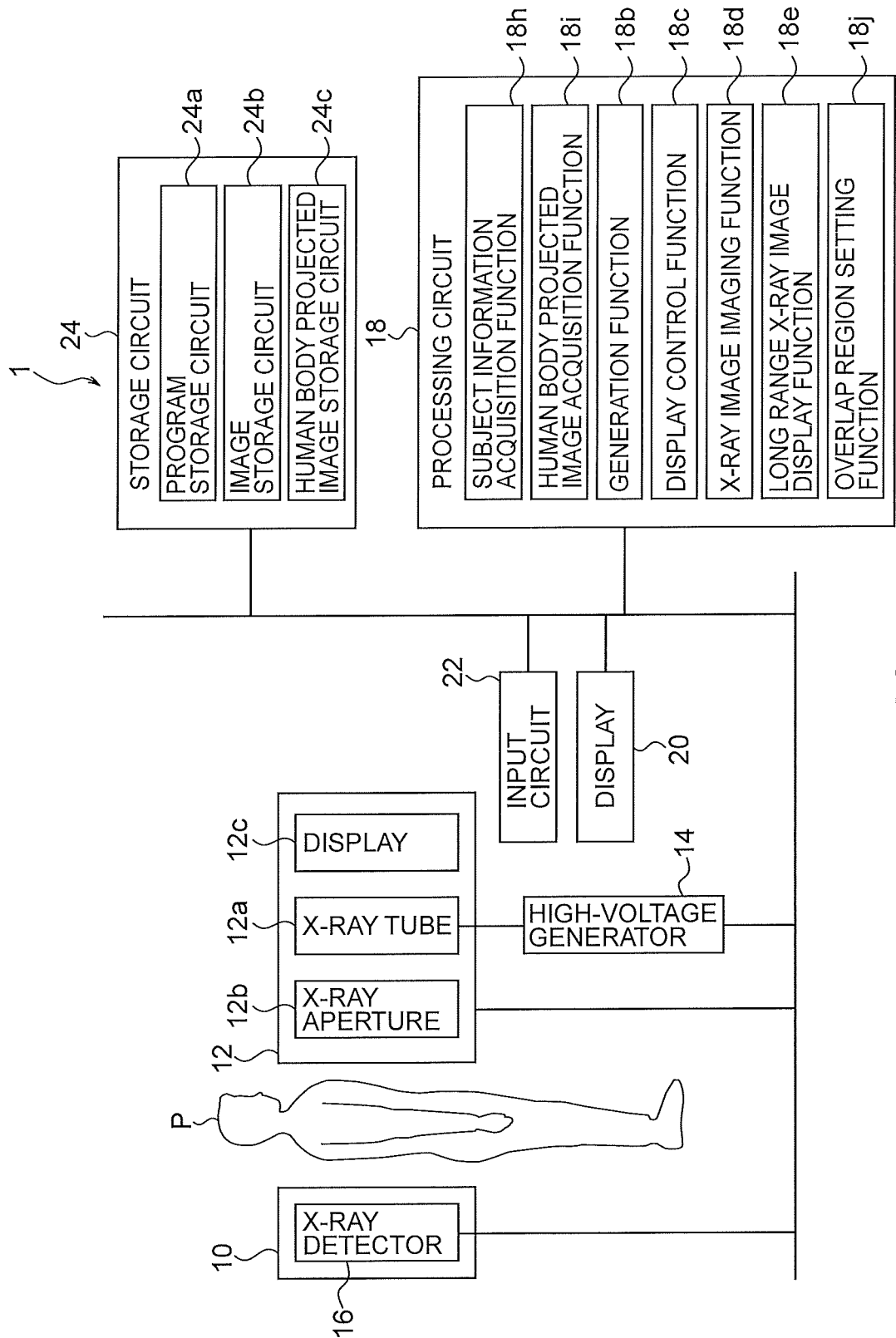
FIG. 26 is a block diagram explaining an entire configuration of an X-ray diagnostic apparatus according to a fifth embodiment (a case of standing position)
Figure 27:
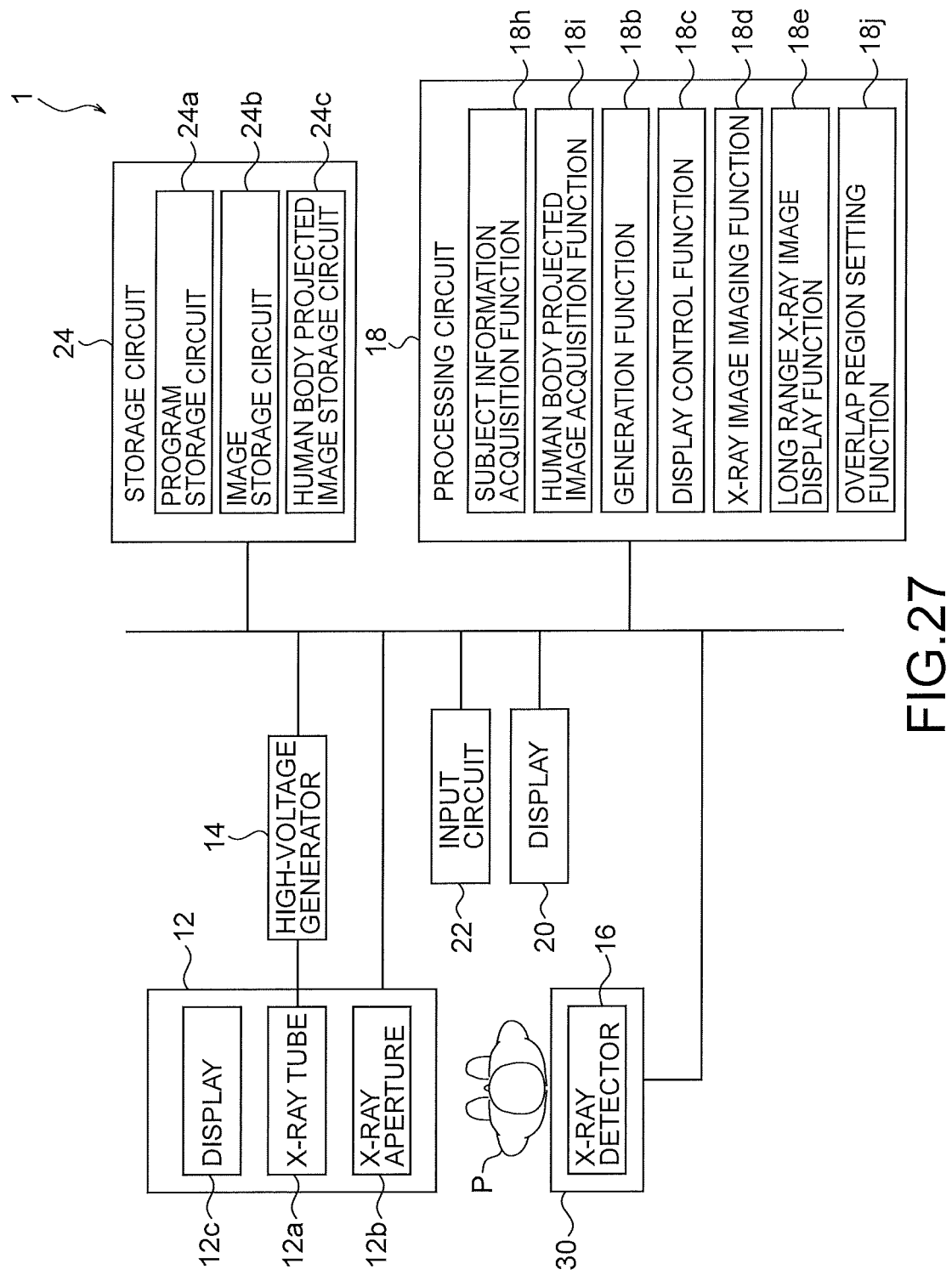
FIG. 27 is a block diagram explaining the entire configuration of the X-ray diagnostic apparatus according to the fifth embodiment (a case of dorsal position)

FIG. 26 is a block diagram explaining an entire configuration of the X-ray diagnostic apparatus 1 according to the fifth embodiment. As illustrated in FIG. 26, in the X-ray diagnostic apparatus 1 according to the present embodiment, an overlap region setting function 18j is further provided in an additional manner to the processing circuit 18. The same applies to the X-ray diagnostic apparatus 1 illustrated in FIG. 27 which performs X-ray imaging of the subject P in a dorsal position. Further, similarly to the above-described fourth embodiment, the X-ray diagnostic apparatus 1 illustrated in each of FIG. 26 and FIG. 27 is connected to the patient information system 110 in a communicable manner.

Figure 28:
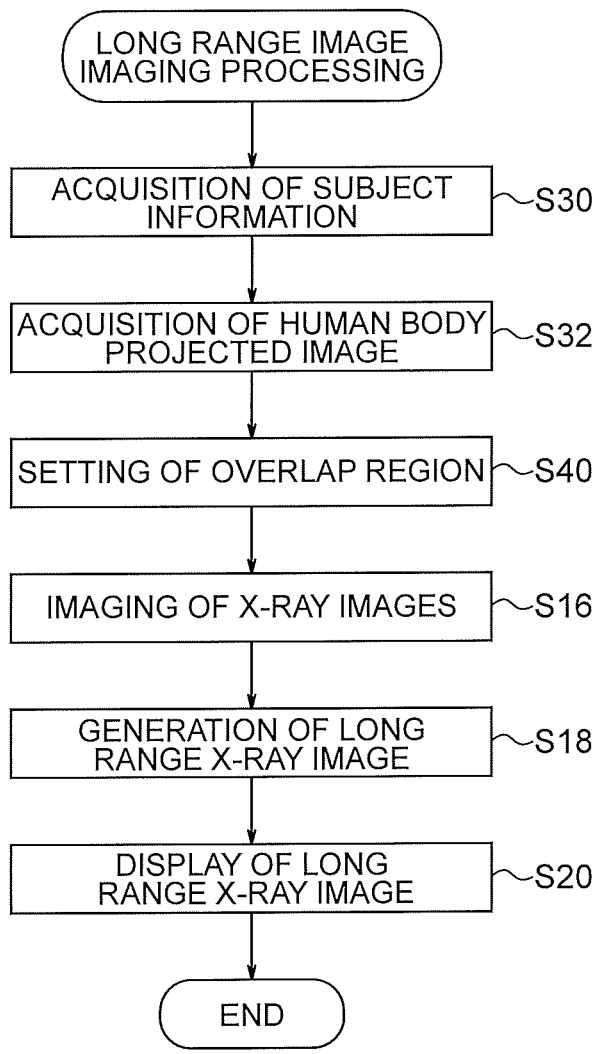
FIG. 28 is a diagram illustrating a flow chart that explains the long range image imaging processing executed by the X-ray diagnostic apparatus in each of FIG. 26 and FIG. 27.

Next, long range image imaging processing which is executed by the X-ray diagnostic apparatus 1 according to the present embodiment will be described based on FIG. 28. The long range image imaging processing illustrated in FIG. 28 is processing which is realized when the processing circuit 18 reads and executes a long range image imaging processing program stored in the program storage circuit 24a of the storage circuit 24. Further, the long range image imaging processing illustrated in FIG. 28 is processing corresponding to the long range image imaging processing illustrated in FIG. 24 in the above-described fourth embodiment.

The processing in step S30 and step S32 in FIG. 28 is similar to that of the above-described fourth embodiment. Subsequently, the X-ray diagnostic apparatus 1 sets an overlap region (step S40). Specifically, an overlap region where two X-ray images are superimposed is set so as to avoid the avoidance region AP being the region of interest in the subject P. The processing of setting the overlap region is realized by the overlap region setting function 18j of the processing circuit 18.

For example, information regarding the avoidance region AP can be acquired from the patient information system 110 as one piece of information regarding the subject P in step S30. Specifically, when a doctor performs imaging of a long range X-ray image, examination information thereof is registered in the patient information system 110 as one piece of information regarding the subject P. This examination information also includes information regarding an imaging region which is regarded as important when a doctor makes a diagnosis. For this reason, the X-ray diagnostic apparatus 1 acquires the information regarding the imaging region from the patient information system 110, and sets the overlap region by avoiding the imaging region being the region of interest for the doctor.

For example, when the imaging region is the large intestine, it is possible to estimate an approximate position of the large intestine based on the information regarding the stature of the subject P. Accordingly, the position of the large intestine which is determined based on the estimation is set to the avoidance region AP. Subsequently, the overlap region is set by avoiding the avoidance region AP being the position of the large intestine. If the age, the sex, the race, and so on in addition to the stature of the subject P are taken into consideration when estimating the position of the imaging region, it becomes possible to further increase the accuracy of the estimation.

By automatically setting the overlap region based on the information regarding the subject P stored in the patient information system 110 in a manner as described above, it is possible to lighten the burden of operation on the operator who operates the X-ray diagnostic apparatus 1. Specifically, when performing imaging of the long range X-ray image, it is possible to save time for operating the preparation screen W1 to move or adjust the overlap region.

Figure 29:
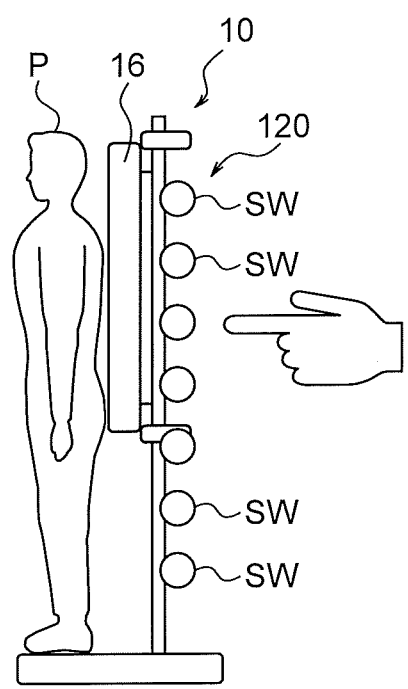
FIG. 29 is a diagram explaining a configuration in which a region designation device is installed in a stand which is provided with an X-ray detector.

Further, in the present embodiment, it is also possible to design such that a region designation device 120 is installed in the stand 10 to which the X-ray detector 16 is provided, to thereby allow the operator to designate the avoidance region AP being the region of interest in the subject P, as illustrated in FIG. 29. Specifically, it is possible to design such that before performing the imaging of the long range X-ray image, the operator of the X-ray diagnostic apparatus 1 operates the region designation device 120 to designate the avoidance region AP and inputs the avoidance region AP into the X-ray diagnostic apparatus 1.

The region designation device 120 is provided with a plurality of designation switches SW. Although the number of the designation switches SW is arbitrary, it is desirable that the designation switches SW can be arranged at a distribution density which is dense enough to be able to designate a region in which a doctor is interested with no large error, regardless of the stature of the subject P. Note that the region designation device 120 is not limited to be configured by the plurality of designation switches SW. For example, it is also possible to design such that a touch panel with a length which is about the same as the stature of the subject P is installed in the stand 10, and the operator designates the avoidance region AP by using the touch panel.

Figure 30:
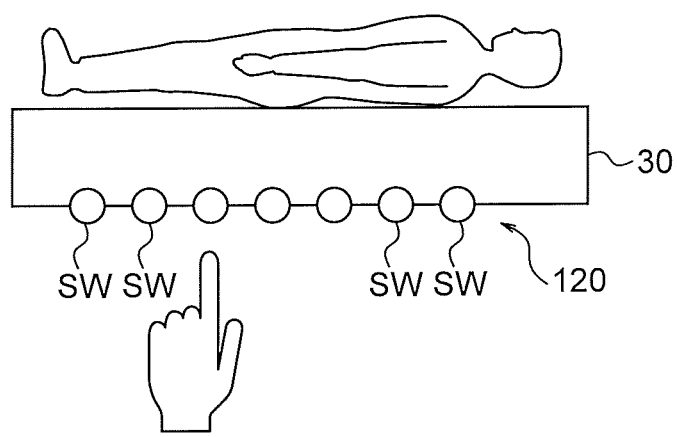
FIG. 30 is a diagram explaining a configuration in which a region designation device is installed in a bed on which a subject lies down.

FIG. 29 illustrates an embodiment in which the region designation device 120 is provided to the X-ray diagnostic apparatus 1 in FIG. 26 which performs the imaging of the X-ray image regarding the standing subject P, but, the region designation device 120 can also be provided to the X-ray diagnostic apparatus 1 in FIG. 27 which performs the imaging of the X-ray image regarding the subject P in a dorsal position. An embodiment in this case is illustrated in FIG. 30. Specifically, the region designation device 120 is provided to a side surface of the bed 30 on which the subject P lies down, and the operator designates the avoidance region AP by using the designation switch SW of the region designation device 120. Also in this case, the region designation device 120 may designate the avoidance region AP through another method such as a touch panel.

By designating the avoidance region AP by using the region designation device 120 as described above, the operator can easily designate the avoidance region AP also in the X-ray diagnostic apparatus 1 in which the optical camera 12d is not provided. Specifically, it is possible to designate the avoidance region AP, namely, it is possible to designate the position at which the overlap region should be avoided, with high accuracy, while seeing the subject P standing in front of the stand 10 or the subject P who lies down on the bed 30.

Figure 31:
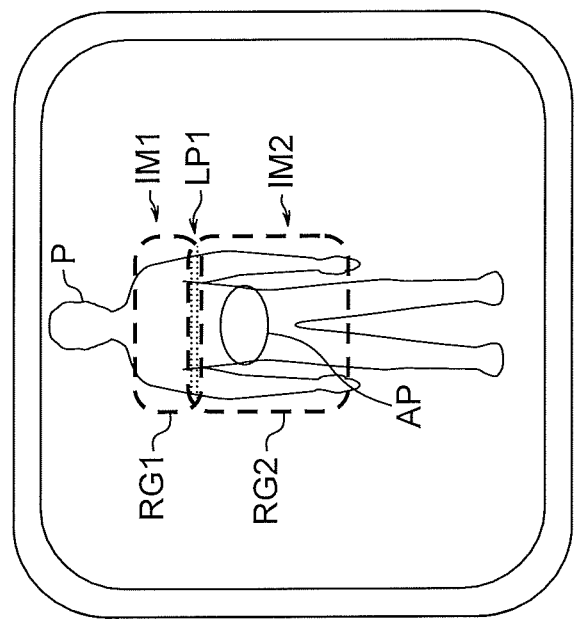
FIG. 31 is a diagram illustrating one example of a preparation screen displayed on a display of the X-ray diagnostic apparatus by step S40 of the long range image imaging processing according to the fifth embodiment.

FIG. 31 is a diagram illustrating one example of the preparation screen W1 which is displayed on the display 12c or the display 20 in step S40. As illustrated in FIG. 31, the X-ray diagnostic apparatus 1 sets the overlap region LP1 between the X-ray image IM1 and the X-ray image IM2 so as to avoid the avoidance region AP being the region of interest. Note that this preparation screen W1 may not be necessarily displayed since it is only displayed on the display 12c or the display 20 for the confirmation for the operator. Further, it is also possible to design such that the operator can additionally adjust the position of the overlap region LP1 by operating the preparation screen W1 according to need.

Next, as illustrated in FIG. 28, the X-ray diagnostic apparatus 1 performs imaging of X-ray images at plural different locations in accordance with the overlap region set in step S40, and generates a long range X-ray image (step S16). The processing of step S16 and thereafter is similar to that of the above-described fourth embodiment.

As described above, according to the X-ray diagnostic apparatus 1 according to the present embodiment, it is possible to set the overlap region LP1 so as to avoid the avoidance region AP being the region of interest and perform the imaging of the long range X-ray image without using the optical camera 12d. Further, by automatically setting the overlap region LP1 based on the information regarding the subject P stored in the patient information system 110, it is possible to lighten the burden of operation on the operator. Alternatively, by designating the avoidance region AP by using the region designation device 120, the operator can easily designate the avoidance region AP while seeing the subject P.

Sixth Embodiment

Although the above-described fifth embodiment is designed such that the avoidance region AP being the region of interest is set, to thereby set the overlap region so as to avoid the avoidance region AP, a sixth embodiment is designed such that the overlap region itself is designated. Hereinafter, a part different from that of the above-described fifth embodiment will be described.

An entire configuration of the X-ray diagnostic apparatus 1 according to the sixth embodiment is similar to that of FIG. 26 and FIG. in the fifth embodiment described above. Further, a configuration of the region designation device 120 is also similar to that of FIG. 29 and FIG. 30 in the fifth embodiment described above. However, processing contents in step S40 in the long range image imaging processing illustrated in FIG. 28 are different.

Specifically, in step S40, the X-ray diagnostic apparatus 1 sets the overlap region of the plurality of X-ray images, and in the present embodiment, the overlap region itself is designated, so that the overlap region of the long range X-ray image is set in accordance with the designation. For example, when the set position of the overlap region is previously registered in the patient information system 110, the X-ray diagnostic apparatus 1 acquires information regarding the set position of the overlap region from the patient information system 110. In this case, for example, a doctor personally sets the overlap region so as to avoid the region of interest, and registers the overlap position in the patient information system 110 as examination information. The X-ray diagnostic apparatus 1 sets the overlap region of the long range X-ray image based on the set position of the overlap region registered in the patient information system 110.

Further, as illustrated in FIG. 29 and FIG. 30, it is also possible that the operator operates the region designation device 120 to designate the overlap region itself. In this case, the operator designates the position of the overlap region by using the designation switch SW of the region designation device 120 so as to avoid the avoidance region AP being the region of interest. Specifically, by operating any of the designation switches SW, the position for avoiding the avoidance region AP is input into the X-ray diagnostic apparatus 1. It is up to the operator regarding that the overlap region is set to which position to avoid the avoidance region AP.

Figure 32:
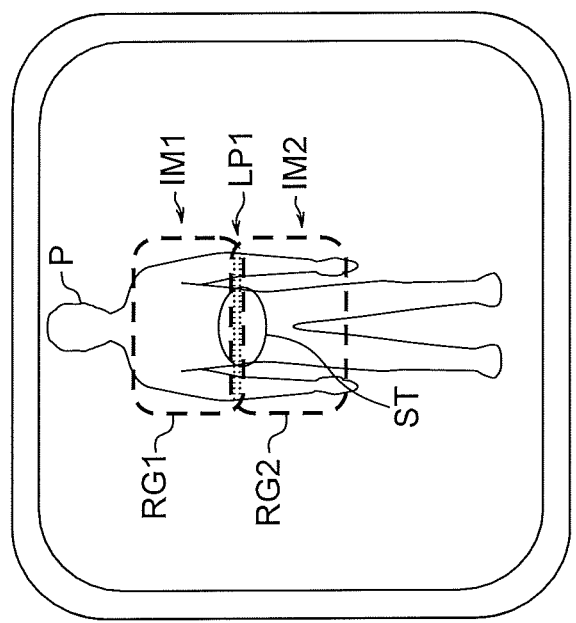
FIG. 32 is a diagram illustrating one example of a preparation screen displayed on a display of an X-ray diagnostic apparatus by step S40 of long range image imaging processing according to a sixth embodiment.

FIG. 32 is a diagram illustrating one example of the preparation screen W1 which is displayed on the display 12c or the display 20 in step S40. In the example of FIG. 32, a position of the overlap region LP1 set by the operator is indicated as a set position ST. The X-ray diagnostic apparatus 1 sets the overlap region LP1 between the X-ray image IM1 and the X-ray image IM2 at the set position ST. Note that this preparation screen W1 may not be necessarily displayed since it is only displayed on the display 12c or the display 20 for the confirmation for the operator. Further, it is also possible to design such that the operator of the X-ray diagnostic apparatus 1 can additionally adjust the position of the overlap region LP1 by operating the preparation screen W1 according to need.

As described above, also in the X-ray diagnostic apparatus 1 according to the present embodiment, it is possible to set the overlap region LP1 by avoiding the avoidance region AP being the region of interest and perform the imaging of the long range X-ray image without using the optical camera 12d. Further, by automatically setting the overlap region LP1 based on the information regarding the set position stored in the patient information system 110, it is possible to lighten the burden of operation on the operator. Alternatively, by designating the set position ST of the overlap region LP1 by using the region designation device 120, the operator can easily set the overlap region LP1 at the position which avoids the avoidance region AP while seeing the subject P.

Although some embodiments have been described above, these embodiments are presented by way of examples only, and are not intended to limit the scope of the invention. The novel apparatuses and methods described in the present description can be implemented in other various forms. Further, the forms of the apparatuses and the methods described in the present description can be omitted, substituted, or changed in various ways within the scope which does not depart from the gist of the invention. The attached claims and the scope equivalent thereto are intended to include such forms and modified examples included in the scope and the gist of the invention.

For example, in the above-described respective embodiments, it is designed such that the display 12c or the display 20 is configured by the touch panel, and the operator performs the various kinds of inputs with respect to the preparation screen W1 through the display 12c or the display 20, but, the various kinds of inputs with respect to the preparation screen W1 are not limited to be performed through the touch panel, and can be performed through an arbitrary method. For example, an input device such as a mouse that operates the display 12c or the display 20 is prepared, and the operator may input various kinds of information with respect to the preparation screen W1 into the X-ray diagnostic apparatus 1 by using this input device.

Further, in the above-described respective embodiments, it is designed such that the preparation screen W1 is displayed on the display 12c or the display 20 of the X-ray tube holding device 12, but, the preparation screen W1 is not limited to be displayed on the display 12c or the display 20, and can be displayed on an arbitrary place. For example, it is also possible to design such that the preparation screen W1 is displayed on a display of a not-illustrated external computer, and the operator performs various kinds of inputs with respect to the preparation screen W1 while seeing this display. If such a configuration is employed, the X-ray diagnostic apparatus 1 is configured as a whole including the external computer and display.

Figure 20:
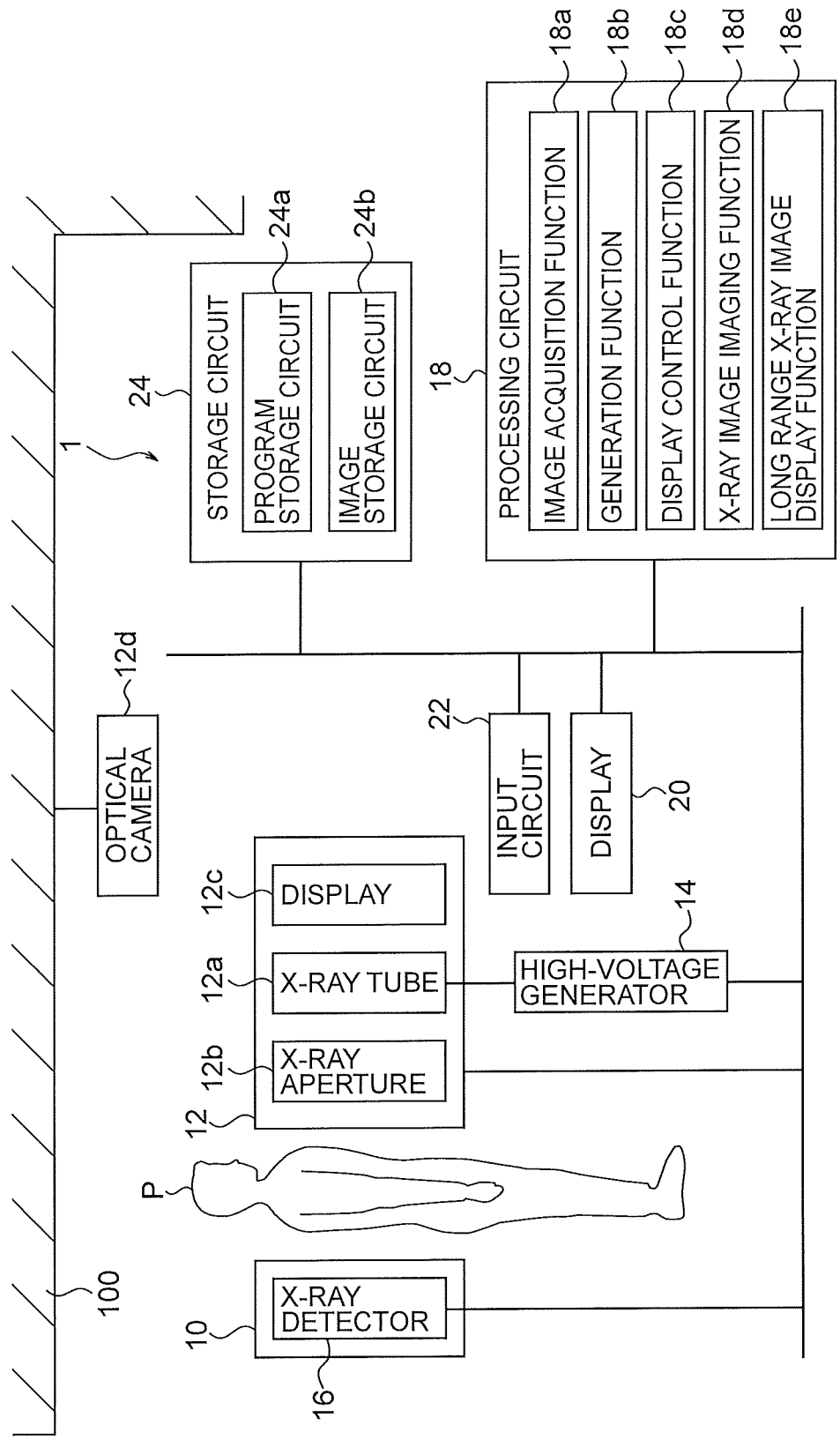
FIG. 20 is a block diagram explaining an entire configuration of an X-ray diagnostic apparatus in a modified example in which an optical camera is attached to a fixture.

Further, although the above-described embodiments describe the example in which the optical camera 12 is provided to the X-ray tube holding device 12, the attachment position of the optical camera 12d is arbitrary. For example, it is also possible to attach the optical camera 12d to a fixture 100 such as a ceiling or a wall, as illustrated in FIG. 20.

The invention claimed is:

1. An X-ray diagnostic apparatus, comprising:
a display configured to superimpose and display a plurality of X-ray irradiation ranges for generating a long range X-ray image on an image indicating a subject; and
a display controller configured to change a position of an overlap region which is displayed on the display and at which the X-ray irradiation ranges which are adjacent to each other are overlapped,
wherein the display controller accepts an operation of a user on the overlap region and changes the position or the size of the overlap region according to whether the operation is a first operation or a second operation.

2. The X-ray diagnostic apparatus according to claim 1, wherein the display controller changes a size of the overlap region based on the operation of the user.

3. The X-ray diagnostic apparatus according to claim 1, wherein the display controller increases a size of one of the X-ray irradiation ranges which are adjacent to each other and decreases a size of the other of the X-ray irradiation range based on the operation of changing the position of the overlap region.

4. The X-ray diagnostic apparatus according to claim 1, further comprising an X-ray image region divider configured to divide the X-ray irradiation range which exceeds a previously determined range based on the operation of changing the X-ray irradiation range or the position of the overlap region.

5. The X-ray diagnostic apparatus according to claim 1, further comprising a first overlap region mover configured to move, based on an operation of designating an avoidance region on an image indicating the subject, the overlap region to a position which avoids the avoidance region when the avoidance region is positioned at the overlap region.

6. The X-ray diagnostic apparatus according to claim 1, wherein the display controller limits the change of the size of the overlap region in order to prevent the overlap region from becoming smaller than a predetermined size based on the operation of changing the size of the overlap region.

7. The X-ray diagnostic apparatus according to claim 1, wherein the display controller limits the size of the X-ray irradiation range including the overlap region in order to prevent the size of the X-ray irradiation range including the overlap region from exceeding a previously determined range based on the operation of changing the position of the overlap region.

8. The X-ray diagnostic apparatus according to claim 1, further comprising a second overlap region mover configured to display, based on an operation of designating an avoidance region on the image indicating the subject, the overlap region at a position which avoids the avoidance region.

9. The X-ray diagnostic apparatus according to claim 1, further comprising an X-ray image imager configured to perform imaging of a long range X-ray image of the subject based on a plurality of X-ray irradiation ranges having the overlap region changed by the display controller.

10. The X-ray diagnostic apparatus according to claim 9, wherein the X-ray image imager controls an X-ray tube to perform a plurality of times of X-ray irradiation based on a plurality of locations at which the overlap region is set.

11. The X-ray diagnostic apparatus according to claim 1, further comprising an optical camera configured to perform imaging of the subject.

12. The X-ray diagnostic apparatus according to claim 1, wherein the display is configured by a touch panel, and an operating input of changing the position of the overlap region by moving the overlap region displayed on the display while dragging the overlap region on the touch panel is accepted.

13. The X-ray diagnostic apparatus according to claim 1, wherein the display controller changes a number of the X-ray irradiation ranges according to the changing of the position of the overlap region.

14. The X-ray diagnostic apparatus according to claim 1, wherein the display controller restricts the change of the position of the overlap region so that a size of the X-ray irradiation range does not become smaller than a predetermined range.

15. The X-ray diagnostic apparatus according to claim 1, wherein the operation of the user is a touch operation on the display and the display controller is configured to identify whether the touch operation is the first operation or the second operation.

16. The X-ray diagnostic apparatus according to claim 15, wherein:
   when the overlap region displayed on the display is touched and dragged on the display, the display controller identifies the touch operation as the first operation and changes the position of the overlap region, and
   when the overlap region displayed on the display is pressed and held, the display controller identifies the touch operation as the second operation and changes the size of the overlap region.

17. An X-ray diagnostic apparatus, comprising:
   an X-ray tube configured to generate X-rays;
   an X-ray detector configured to detect the X-rays transmitted through a subject;
   a display configured to superimpose and display a plurality of X-ray irradiation ranges on an image indicating the subject;
   an input accepter configured to accept an operation of a user; and
   a display controller configured to change at least one of a position and a size of an overlap region which is displayed on the display and at which the X-ray irradiation ranges which are adjacent to each other are overlapped,
   wherein, the display controller accepts an operation of a user on the overlap region and changes the position or the size of the overlap region according to whether the operation is a first operation or a second operation.

* * * * *